Figure 1:
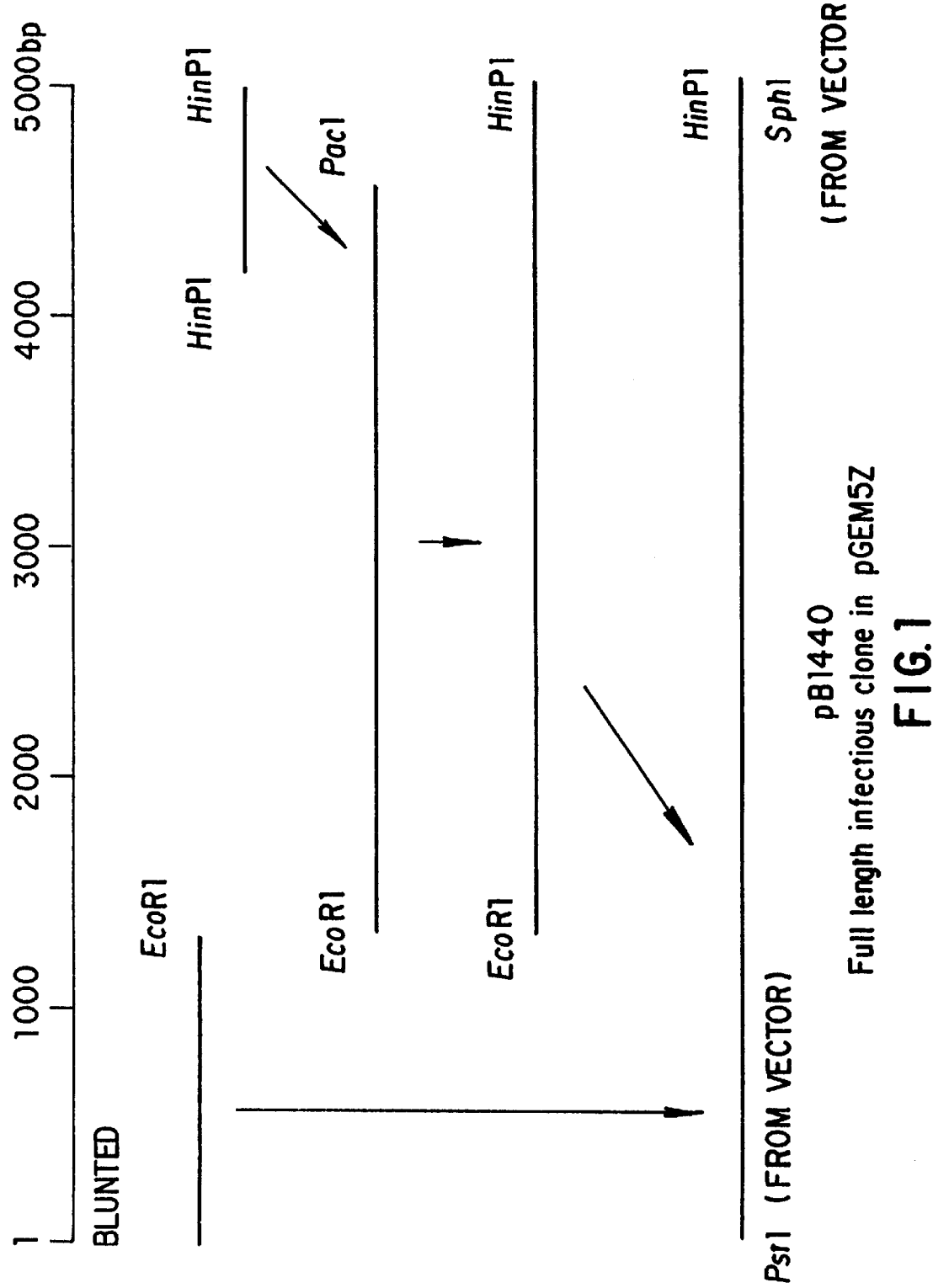

United States Patent [19]
Parrish et al.

[11] Patent Number: 5,885,585
[45] Date of Patent: Mar. 23, 1999

[54] ATTENUATED CANINE PARVOVIRUS VACCINE

[75] Inventors: Colin R. Parrish; Leland E. Carmichael, both of Ithaca, N.Y.; Allen Gruenberg, Wellington, New Zealand

[73] Assignee: Cornell Research Foundation, Inc., Ithaca, N.Y.

[21] Appl. No.: 647,655

[22] Filed: May 15, 1996

Related U.S. Application Data

[63] Continuation-in-part of Ser. No. 336,345, Nov. 8, 1994, Pat. No. 5,814,510.
[51] Int. Cl.$^6$ .............................. A61K 39/12; C12N 7/00; C12N 7/04; C07H 21/04
[52] U.S. Cl. .................................. 424/204.1; 424/186.1; 435/235.1; 435/236; 536/23.72
[58] Field of Search .............................. 424/186.1, 204.1; 435/235.1, 236; 536/23.72

[56] References Cited

U.S. PATENT DOCUMENTS

| | | | |
|---|---|---|---|
| 4,193,990 | 3/1980 | Appel et al. | 424/89 |
| 4,193,991 | 3/1980 | Appel et al. | 424/89 |
| 4,303,645 | 12/1981 | Carmichael et al. | 424/89 |
| 4,810,494 | 3/1989 | Welsh | 424/89 |
| 4,971,793 | 11/1990 | Wood et al. | 424/88 |

FOREIGN PATENT DOCUMENTS 554 414 A2  11/1993  European Pat. Off. .

OTHER PUBLICATIONS

Parrish et al., Rapid Antigen–Type Replacement and DNA Sequence Evolution of Canine Parvovirus, J. Virol., vol. 65, No. 12, pp. 6544–6552, see p. 6545, left column , p. 6544, column 2, second full paragraph), Dec. 1991.

Parrish, Emergence, Natural History, and Variation of Canine, Mink, and Feline Parvoviruses, Adv. Virus Res. 38:403–450, see pp. 419–423, 1990.

Gruenberg et al., 1993, "Preparation and analysis of a molecular clone of an attenuated strain of canine parvovirus" Abstract, 5th Parvovirus Workshop, Nov. 10–14, 1993, Cyrstal River, Florida.

Lopez de Turison et al., 1992, "Recombinant vaccine for canine parvovirus in dogs", J Virol 66(5):2748–2753.

Saliki et al., 1992, "Canine parvovirus empty capsids produced by expression in a baculovirus vector: Use in analysis of viral properties and immunization of dogs", J Gen Virol 73:369–374.

Parrish et al., 1991 "Mapping specific functions in the capsid structure of canine parvovirus and feline panleukipenia virus using infectious plasmid clones", Virology 183:195–205.

Parrish et al., 1991, "Rapid antigenic–type replacement and DNA sequence evolution of canine parvovirus", J Virol 65(12):6544–6552.

Parrish, 1990, "Emergence, natural history, and variation of canine, mink, and feline parvovirus", Adv Virus Res 38:403–450.

Ausubel et al., 1989, Current Potocols in Molecular Biology, Greene Publshing Associates and Wiley Interscience, Chapter 8.

Chang et al., 1988, "Multiple amino acids in the capsid structure of canine parvovirus coordinately determine the canine host range and specific antigenic and hemagglutination properties", J Virol 66(12):6858–6867.

(List continued on next page.)

*Primary Examiner*—Ponnathapura Achutamurthy
*Assistant Examiner*—Hankyel T. Park
*Attorney, Agent, or Firm*—Pennie & Edmonds LLP

[57] ABSTRACT

The invention is directed to attenuated canine parvovirus (CPV) strains which may be used as a veterinary vaccine against CPV disease. The invention is further directed to a virus stock generated from a genomic DNA clone of the attenuated CPV strain which is used as a veterinary vaccine and is able to confer protective immunity to dogs against challenge with virulent CPV. Methods are given for the production of an attenuated CPV virus from a cloned CPV genome which may be used as a veterinary vaccine.

12 Claims, 12 Drawing Sheets

OTHER PUBLICATIONS

Mazzara et al., 1987, "Successful vaccination of dogs with empty capsids derived from canine parvovirus–bovine papillomavirus chimeric plasmids", Vaccines 87, Cold Spring Harbor Laboratory Press, pp. 419–424.

Botstein and Shortle, 1985, "Strategies and applications of in vitro mutagenesis", Science 229:1193–1201.

Parrish et al., 1984, "Characterization of antigenic variation among mink enteritis virus isolates", Am J Vet Res 45:2591–2599.

Zoller and Smith, 1984, "Oligonucleotide–directed mutagenesis: A simple method using two oligonucliotide primers and a single stranded DNA template", DNA 3(6):479–488.

Carmichael et al., 1983, "A modified live canine parvovirus vaccine II. Immune Response", Cornell Vet 73:13–29.

Carmichael et al. 19881, "A modified live canine parvovirus strain with novel plaque characteristics I. Viral attenuation and dog response", Cornell Vet 71:408–427.

Carmichael et al., 1980 "Hemagglutination by canine parvovirus: Serologic studies and diagnostic applications", Am J Vet Res 41(5):784–791.

Appel et al., 1979, "Isolation and immunisation studies of a canine parvo–like virus from dogs with haemorrhagic enteritis", Vet Record 105:156–159.

Bovarnick et al., 1950, "The influence of certain salts, amino acids, sugars, and proteins on the stability of rickettsiae", J Bact 59:509–522.

Gruenberg et al., 1993, Poster Panels from an oral presentation given at the Fifth Parvovirus Workshop, Crystal City, Florida, Nov. 10–14, 1993.

Churchill, 1987, "Preliminary Devleopment of a Live Attenuated Canine Parvovirus Vaccine from an isloate of British origin", The Veterinary Record 120:334–339.

pB1440
Full length infectious clone in pGEM5Z

| | |
|---|---|
| ATCATTCTTT AGAACCAACT GACCAAGTTC ACGTACGTAT GACGTGATGA CGCGCGCTAC | 60 |
| GCGCGCTGCC TACGGCAGTC ACACGTCATA CGTACGTTCC TTGGTCAGTT GGTTCTAAAG | 120 |
| AATGATAGGC GGTTTGTGTG TTTAAACTTG GGCGGGAAAA GGTGGCGGGC TAATTGTGGG | 180 |
| CGTGGTTAAA GGTATAAAAG ACAAACCATA GACCGTTACT GACATTCGCT TCTTGTCTTT | 240 |
| GACAGAGTGA ACCTCTCTTA CTTTGACTAA CCATGTCTGG CAACCAGTAT ACTGAGGAAG | 300 |
| TTATGGAGGG AGTAAATTGG TTAAAGAAAC ATGCAGAAAA TGAAGCATTT TCGTTTGTTT | 360 |
| TTAAATGTGA CAACGTCCAA CTAAATGGAA AGGATGTTCG CTGGAACAAC TATACCAAAC | 420 |
| CAATTCAAAA TGAAGAGCTA ACATCTTTAA TTAGAGGAGC ACAAACAGCA ATGGATCAAA | 480 |
| CCGAAGAAGA AGAAATGGAC TGGGAATCGG AAGTTGATAG TCTCGCCAAA AAGCAAGTAC | 540 |
| AAACTTTTGA TGCATTAATT AAAAAAATGTC TTTTTGAAGT CTTTGTTTCT AAAAATATAG | 600 |
| AACCAAATGA ATGTGTTTGG TTTATTCAAC ATGAATGGGG AAAAGATCAA GGCTGGCATT | 660 |
| GTCATGTTTT ACTTCATAGT AAGAACTTAC AACAAGCAAC TGGTAAATGG CTACGCAGAC | 720 |
| AAATGAATAT GTATTGGAGT AGATGGTTGG TGACTCTTTG TTCGGTAAAC TTAACACCRA | 780 |
| CTGAAAAGAT TAAGCTCAGA GAAATTGCAG AAGATAGTGA ATGGGTGACT ATATTAACAT | 840 |
| ACAGACATAA GCAAACAAAA AAAGACTATG TTAAAATGGT TCATTTTGGA AATATGATAG | 900 |
| CATATTACTT TTTAACAAAG AAAAAAATTC TCCACATGAC AAAAGAAAGT GGCTATTTTT | 960 |
| TAAGTACTGA TTCTGGTTGG AAATTTAACT TTATGAAGTA TCAAGACAGA CAAATTGTCA | 1020 |
| GCRCACTTTA CACTGAACAA ATGAAACCAG AAACCGTTGA ACCACAGTG ACGACAGCAC | 1080 |
| AGGAAACAAA GCGCGGGAGA ATTCAAACTA AAAAGGAAGT GTCAATCAAA TGTACTTTGC | 1140 |
| GGGACTTGGT TAGTAAAAGA GTAACATCAC CTGAAGACTG GATGATGTTA CAACCAGATA | 1200 |

FIG.3A

| | |
|---|---|
| GTTATATTGA AATGATGGCA CAACCAGGAG GTGAAAATCT TTTAAAAAAT ACACTTGAAA | 1260 |
| TTTGTACTTT GACTTTAGCA AGAACAAAAA CAGCATTTGA ATTAATACTT GAAAAAGCAG | 1320 |
| ATAATACTAA ACTAACTAAC TTTGATCTTG CAAATTCTAG AACATGTCAA ATTTTTAGAA | 1380 |
| TGCACGGATG GAATTGGATT AAAGTTTGTC ACGCTATAGC ATGTGTTTTA AATAGACAAG | 1440 |
| GTGGTAAAAG AAATACAGTT CTTTTTCATG GACCAGCAAG TACAGGAAAA TCTATCATTG | 1500 |
| CTCAAGCCAT AGCACAAGCT GTGGGTAATG TTGGTTGTTA TAATGCAGCA AATGTAAATT | 1560 |
| TTCCATTTAA TGACTGTACC AATAAAAATT TAATTTGGAT TGAAGAAGCT GGTAACTTTG | 1620 |
| GTCAACAAGT TAATCAATTT AAAGCAATCT GTTCTGGACA AACAATTAGA ATTGATCAAA | 1680 |
| AAGGTAAAGG AAGTAAGCAA ATTGAACCAA CTCCAGTAAT TATGACAACT AATGAAAATA | 1740 |
| TAACAATTGT GAGAATTGGA TGTGAAGAAA GACCTGAACA TACACAACCA ATAAGAGACA | 1800 |
| GAATGTTGAA CATTAAGTTA GTATGTAAGC TTCCAGGAGA CTTTGGTTTG GTTGATAAAG | 1860 |
| AAGAATGGCC TTTAATATGT GCATGGTTAG TTAAACATGG TTTTGAATCA ACCATGGCTA | 1920 |
| ACTATACACA TCATTGGGGA AAAGTACCAG AATGGGATGA AAACTGGGCG GAGCCTAAAA | 1980 |
| TACAAGAAGG TATAAATTCA CCAGGTTGCA AAGACTTAGA GACACAAGCG GCAAGCAATC | 2040 |
| CTCAGAGTCA AGACCAAGTT CTAACTCCTC TGACTCCGGA CGTAGTGGAC CTTGCACTGG | 2100 |
| AACCGTGGAG TACTCCAGAT ACGCCTATTG CAGAAACTGC AAATCAACAA TCAAACCAAC | 2160 |
| TTGGCGTTAC TCACAAAGAC GTGCAAGCGA GTCCGACGTG GTCCGAAATA GAGGCAGACC | 2220 |
| TGAGAGCCAT CTTTACTTCT GAACAATTGG AAGAAGATTT TCGAGACGAC TTGGATTAAG | 2280 |
| GTACGATGGC ACCTCCGGCA AAGAGAGCCA GGAGAGGTAA GGGTGTGTTA GTAAAGTGGG | 2340 |
| GGGAGGGGAA AGATTTAATA ACTTAACTAA GTATGTGTTT TTTTATAGGA CTTGTGCCTC | 2400 |

FIG.3B

| | | | | | |
|---|---|---|---|---|---|
| CAGGTTATAA | ATATCTTGGG | CCTGGGAACA | GTCTTGACCA | AGGAGAACCA | ACTAACCCTT 2460 |
| CTGACGCCGC | TGCAAAAGAA | CACGACGAAG | CTTACGCTGC | TTATCTTCGC | TCTGGTAAAA 2520 |
| ACCCATACTT | ATATTTCTCG | CCAGCAGATC | AACGCTTTAT | AGATCAAACT | AAGGACGCTA 2580 |
| AAGATTGGGG | GGGGAAAATA | GGACATTATT | TTTTTAGAGC | TAAAAAGGCA | ATTGCTCCAG 2640 |
| TATTAACTGA | TACACCAGAT | CATCCATCAA | CATCAAGACC | AACAAAACCA | ACTAAAAGAA 2700 |
| GTAAACCACC | ACCTCATATT | TTCATCAATC | TTGCAAAAAA | AAAAAAAGCC | GGTGCAGGAC 2760 |
| AAGTAAAAAG | AGACAATCTT | GCACCAATGA | GTGATGGAGC | AGTTCAACCA | GACGGTGGTC 2820 |
| AACCTGCTGT | CAGAAATGAA | AGAGCTACAG | GATCTGGGAA | CGGGTCTGGA | GGCGGGGGTG 2880 |
| GTGGTGGTTC | TGGGGGTGTG | GGGATTTCTA | CGGGTACTTT | CAATAATCAG | ACGGAATTTA 2940 |
| AATTTTTGGA | AAACGGATGG | GTGGAAATCA | CAGCAAACTC | AAGCAGACTT | GTACATTTAA 3000 |
| ATATGCCAGA | AAGTGAAAAT | TATAGAAGAG | TGGTTGTAAA | TAATTTGGAT | AAAACTGCAG 3060 |
| TTAACGGAAA | CATGGCTTTA | GATGATACTC | ATGCACAAAT | TGTAACACCT | TGGTCATTGG 3120 |
| TTGATGCAAA | TGCTTGGGGA | GTTTGGTTTA | ATCCAGGAGA | TTGGCAACTA | ATTGTTAATA 3180 |
| CTATGAGTGA | GTTGCATTTA | GTTAGTTTTG | AACAAGAAAT | TTTTAATGTT | GTTTTAAAGA 3240 |
| CTGTTTCAGA | ATCTGCTACT | CAGCCACCAA | CTAAAGTTTA | TAATAATGAT | TTAACTGCAT 3300 |
| CATTGATGGT | TGCATTAGAT | AGTAATAATA | CTATGCCATT | TACTCCAGCA | GCTATGAGAT 3360 |
| CTGAGACATT | GGGTTTTTAT | CCATGGAAAC | CAACCATACC | AACTCCATGG | AGATATTATT 3420 |
| TTCAATGGGA | TAGAACATTA | ATACCATCTC | ATACTGGAAC | TAGTGGCACA | CCAACAAATA 3480 |
| TATACCATGG | TACAGATCCA | GATGATGTTC | AATTTTATAC | TATTGAAAAT | TCTGTGCCAG 3540 |
| TACACTTAcT | AAGAACAGGT | GATGAATTTG | CTACAGGAAC | ATTTTTTTTT | GATTGTAAAC 3600 |

FIG.3C

```
CATGTAGACT AACACATACA TGGCAAACAA ATAGAGCATT GGGCTTACCA CCATTTCTAA    3660

ATTCTTTGCC TCAATCTGAA GGAGGTACTA ACTTTGGTTA TATAGGAGTT CAACAAGATA    3720

AAAGACGTGG TGTAACTCAA ATGGGAAATA CAAACTATAT TACTGAAGCT ACTATTATGA   3780

GACCAGCTGA GGTTGGTTAT AGTGCACCAT ATTATTCTTT TGAGGCGTCT ACACAAGGGC    3840

CATTTAAAAC ACCTATTGCA GCAGGACGGG GGGGAGCGCA AACAGATGAA AATCAAGCAG    3900

CAGATGGTGA TCCAAGATAT GCATTTGGTA GACAACATGG TCAAAAAACT ACCACAACAG    3960

GAGAAACACC TGAGAGATTT ACATATATAG CACATCAAGA TACAGGAAGA TATCCAGAAG    4020

GAGATTGGAT TCAAAATATT AACTTTAACC TTCCTGTAAC AGATGATAAT GTATTGCTAC    4080

CAACAGATCC AATTGGAGGT AAAACAGGAA TTAACTATAC TAATATATTT AATACTTATG    4140

GTCCTTTAAC TGCATTAAAT AATGTACCAC CAGTTTATCC AAATGGTCAA ATTTGGGATA    4200

AAGAATTTGA TACTGACTTA AAACCAAGAC TTCATGTAAA TGCACCATTT GTTTGTCAAA    4260

ATAATTGTCC TGGTCAATTA TTTGTAAAAG TTGCGCCTAA TTTAACAAAT GAATATGATC    4320

CTGATGCATC TGCTAATATG TCAAGAATTG TAACTTACTC AGATTTTTGG TGGAAAGGTA    4380

AATTAGTATT TAAAGCTAAA CTAAGAGCCT CTCATACTTG GAATCCAATT CAACAAATGA    4440

GTATTAATGT AGATAACCAA TTTAACTATG TACCAAGTAA TATTGGAGGT ATGAAAATTG    4500

TATATGAAAA ATCTCAACTA GCACCTAGAA AATTATATTA ACATACTTAC TATGTTTTTA    4560

TGTTTATTAC ATATCAACTA GCACCTAGAA AATTATATTA ATATACTTAC TATGTTTTTA    4620

TGTTTATTAC ATATTATTTT AAGATTAATT AAATTACAGC ATAGAAATAT TGTACTTGTA    4680

TTTGATATAG GATTTAGAAG GTTTGTTATA TGGTATACAA TAACTGTAAG AAATAGAAGA    4740

ACATCTAGAT CATAGTTAGT AGTTTGTTTT ATAAAATGTA TTGTAAACCA TTAATGTATG    4800
```

FIG.3D

```
TTGTTATGGT GTGGGTGGTT GGTTGGTTTG CCCTTAGAAT ATGTTAAGGA CCAAAANAkA    4860

TCAATAAAAG ACATTTAAAA TTAAATGGCC TCGTATACTG TCTATAAGGT GAACTAACCT    4920

TACCATAAGT ATCAATCTGT CTTTAAGGGG GGGGTGGGTG GGAGATGCAC AACATCAGTA    4980

GACTGACTGG CCTGGTTGGT TGCTCTGCTT AATCAACCAG ACCGCGTAGC GGTCTGGTTG    5040

ATTAAGCGC                                                           5049
```

FIG.3E

```
ATCATTCTTT AGAACCAACT GACCAAGTTC ACGTACGTAT GACGTGATGA CGCGCGCTGC   60
GCGCGCTGCC TACGGCAGTC ACACGTCATA CGTACGCTCC TTGGTCAGTT GGTTCTAAAG  120
AATGATAGGC GGTTTGTGTG TTTAAACTTG GGCGGGAAAA GGTGGCGGGC TAATTGTGGG  180
CGTGGTTAAA GGTATAAAAG ACAAACCATA GACCGTTACT GACATTCGCT TCTTGTCTTT  240
GACAGAGTGA ACCTCTCTTA CTTTGACTAA CCATGTCTGG CAACCAGTAT ACTGAGGAAG  300
TTATGGAGGG AGTAAATTGG TTAAAGAAAC ATGCAGAAAA TGAAGCATTT TCGTTTGTTT  360
TTAAATGTGA CAACGTCCAA CTAAATGGAA AGGATGTTCG CTGGAACAAC TATACCAAAC  420
CAATTCAAAA TGAAGAGCTA ACATCTTTAA TTAGAGGAGC ACAAACAGCA ATGGATCAAA  480
CCGAAGAAGA AGAAATGGAO TGGGAATCGG AAGTTGATAG TCTCGCCAAA AAGCAAGTAC  540
AAACTTTTGA TGCATTAATT AAAAAATGTC TTTTTGAAGT CTTTGTTTCT AAAAATATAG  600
AACCAAATGA ATGTGTTTGG TTTATTCAAC ATGAATGGGG AAAAGATCAA GGCTGGCATT  660
GTCATGTTTT ACTTCATAGT AAGAACTTAC AACAAGCAAC TGGTAAATGG CTACGCAGAC  720
AAATGAATAT GTATTGGAGT AGATGGTTGG TGACTCTTTG TTCGGTAAAC TTAACACCAA  780
CTGAAAAGAT TAAGCTCAGA GAAATTGCAG AAGATAGTGA ATGGGTGACT ATATTAACAT  840
ACAGACATAA GCAAACAAAA AAAGACTATG TTAAAATGGT TCATTTTGGA AATATGATAG  900
CATATTACTT TTTAACAAAG AAAAAAATTG TCCACATGAC AAAAGAAAGT GGCTATTTTT  960
TAAGTACTGA TTCTGGTTGG AAATTTAACT TTATGAAGTA TCAAGACAGA CAAATTGTCA 1020
GCACACTTTA CACTGAACAA ATGAAACCAG AAACCGTTGA ACCACAGTG ACGACAGCAC 1080
AGGAAACAAA GCGCGGGAGA ATTCAAACTA AAAAGGAAGT GTCAATCAAA TGTACTTTGC 1140
GGGACTTGGT TAGTAAAAGA GTAACATCAC CTGAAGACTG GATGATGTTA CAACCAGATA 1200
GTTATATTGA AATGATGGCA CAACCAGGAG GTGAAAATCT TTTAAAAAAT ACACTTGAAA 1260
TTTGTACTTT GACTTTAGCA AGAACAAAAA CAGCATTTGA ATTAATACTT GAAAAAGCAG 1320
```

FIG.4A

```
ATAATACTAA ACTAACTAAC TTTGATCTTG CAAATTCTAG AACATGTCAA ATTTTTAGAA   1380
TGCACGGATG GAATTGGATT AAAGTTTGTC ACGCTATAGC ATGTGTTTTA AATAGACAAG   1440
GTGGTAAAAG AAATACAGTT CTTTTTCATG GACCAGCAAG TACAGGAAAA TCTATCATTG   1500
CTCAAGCCAT AGCACAAGCT GTGGGTAATG TTGGTTGTTA TAATGCAGCA AATGTAAATT   1560
TTCCATTTAA TGACTGTACC AATAAAAATT TAATTTGGAT TGAAGAAGCT GGTAACTTTG   1620
GTCAACAAGT TAATCAATTT AAAGCAATCT GTTCTGGACA AACAATTAGA ATTGATCAAA   1680
AAGGTAAAGG AAGTAAGCAA ATTGAACCAA CTCCAGTAAT TATGACAACT AATGAAAATA   1740
TAACAATTGT GAGAATTGGA TGTGAAGAAA GACCTGAACA TACACAACCA ATAAGAGACA   1800
GAATGTTGAA CATTAAGTTA GTATGTAAGC TTCCAGGAGA CTTTGGTTTG GTTGATAAAG   1860
AAGAATGGCC TTTAATATGT GCATGGTTAG TTAAACATGG TTTTGAATCA ACCATGGCTA   1920
ACTATACACA TCATTGGGGA AAAGTACCAG AATGGGATGA AAACTGGGCG GAGCCTAAAA   1980
TACAAGAAGG TATAAATTCA CCAGGTTGCA AAGACTTAGA GACACAAGCG GCAAGCAATC   2040
CTCAGAGTCA AGACCAAGTT CTAACTCCTC TGACTCCGGA CGTAGTGGAC CTTGCACTGG   2100
AACCGTGGAG TACTCCAGAT ACGCCTATTG CAGAAACTGC AAATCAACAA TCAAACCAAC   2160
TTGGCGTTAC TCACAAAGAC GTGCAAGCGA GTCCGACGTG GTCCGAAATA GAGGCAGACC   2220
TGAGAGCCAT CTTTACTTCT GAACAATTGG AAGAAGATTT TCGAGACGAC TTGGATTAAG   2280
GTACGATGGC ACCTCCGGCA AAGAGAGCCA GGAGAGGTAA GGGTGTGTTA GTAAAGTGGG   2340
GGGAGGGGAA AGATTTAATA ACTTAACTAA GTATGTGTTT TTTTATAGGA CTTGTGCCTC   2400
CAGGTTATAA ATATCTTGGG CCTGGGAACA GTCTTGACCA AGGAGAACCA ACTAACCCTT   2460
CTGACGCCCG TGCAAAAGAA CACGACGAAG CTTACGCTGC TTATCTTCGC TCTGGTAAAA   2520
ACCCATACTT ATATTTCTCG CCAGCAGATC AACGCTTTAT AGATCAAACT AAGGACGCTA   2580
AGATTGGGG GGGGAAAATA GGACATTATT TTTTTAGAGC TAAAAAGGCA ATTGCTCCAG   2640
```

FIG.4B

```
TATTAACTGA TACACCAGAT CATCCATCAA CATCAAGACC AACAAAACCA ACTAAAAGAA   2700
GTAAACCACC ACCTCATATT TTCATCAATC TTGCAAAAAA AAAAAAAGCC GGTGCAGGAC   2760
AAGTAAAAAG AGACAATCTT GCACCAATGA GTGATGGAGC AGTTCAACCA GACGGTGGTC   2820
AACCTGCTGT CAGAAATGAA AGAGCTACAG GATCTGGGAA CGGGTCTGGA GGCGGGGGTG   2880
GTGGTGGTTC TGGGGGTGTG GGGATTTCTA CGGGTACTTT CAATAATCAG ACGGAATTTA   2940
AATTTTTGGA AAACGGATGG GTGGAAATCA CAGCAAACTC AAGCAGACTT GTACATTTAA   3000
ATATGCCAGA AAGTGAAAAT TATAGAAGAG TGGTTGTAAA TAATTTGGAT AAAACTGCAG   3060
TTAACGGAAA CATGGCTTTA GATGATACTC ATGCACAAAT TGTAACACCT TGGTCATTGG   3120
TTGATGCAAA TGCTTGGGGA GTTTGGTTTA ATCCAGGAGA TTGGCAACTA ATTGTTAATA   3180
CTATGAGTGA GTTGCATTTA GTTAGTTTTG AACAAGAAAT TTTTAATGTT GTTTTAAAGA   3240
CTGTTTCAGA ATCTGCTACT CAGCCACCAA CTAhAGTTTA TAATAATGAT TTAACTGCAT   3300
CATTGATGGT TGCATTAGAT AGTAATAATA CTATGCCATT TACTCCAGCA GCTATGAGAT   3360
CTGAGACATT GGGTTTTTAT CCATGGAAAC CAACCATACC AACTCCATGG AGATATTATT   3420
TTCAATGGGA TAGAACATTA ATACCATCTC ATACTGGAAC TAGTGGCACA CCAACAAATA   3480
TATACCATGG TACAGATCCA GATGATGTTC AATTTTATAC TATTGAAAAT TCTGTGCCAG   3540
TACACTTACT AAGAACAGGT GATGAATTTG CTACAGGAAC ATTTTTTTTT GATTGTAAAC   3600
CATGTAGACT AACACATACA TGGCAAACAA ATAGAGCATT GGGCTTACCA CCATTTCTAA   3660
ATTCTTTGCC TCAATCTGAA GGAGGTACTA ACTTTGGTTA TATAGGAGTT CAACAAGATA   3720
AAAGACGTGG TGTAACTCAA ATGGGAAATA CAAACTATAT TACTGAAGCT ACTATTATGA   3780
GACCAGCTGA GGTTGGTTAT AGTGCACCAT ATTATTCTTT TGAGGCGTCT ACACAAGGGC   3840
CATTTAAAAC ACCTATTGCA GCAGGACGGG GGGGAGCGCA AACAGATGAA AATCAAGCAG   3900
CAGATGGTGA TCCAAGATAT GCATTTGGTA GACAACATGG TCAAAAAACT ACCACAACAG   3960
```

FIG.4C

```
GAGAAACACC TGAGAGATTT ACATATATAG CACATCAAGA TACAGGAAGA TATCCAGAAG    4020
GAGATTGGAT TCAAAATATT AACTTTAACC TTCCTGTAAC AGATGATAAT GTATTGCTAC    4080
CAACAGATCC AATTGGAGGT AAAACAGGAA TTAACTATAC TAATATATTT AATACTTATG    4140
GTCCTTTAAC TGCATTAAAT AATGTACCAC CAGTTTATCC AAATGGTCAA ATTTGGGATA    4200
AAGAATTTGA TACTGACTTA AAACCAAGAC TTCATGTAAA TGCACCATTT GTTTGTCAAA    4260
ATAATTGTCC TGGTCAATTA TTTGTAAAAG TTGCGCCTAA TTTAACAAAT GAATATGATC    4320
CTGATGCATC TGCTAATATG TCAAGAATTG TAACTTACTC AGATTTTTGG TGGAAAGGTA    4380
AATTAGTATT TAAAGCTAAA CTAAGAGCCT CTCATACTTG GAATCCAATT CAACAAATGA    4440
GTATTAATGT AGATAACCAA TTTAACTATG TACCAAGTAA TATTGGAGGT ATGAkAATTG    4500
TATATGAAAA ATCTCAACTA GCACCTAGAA AATTATATTA ACATACTTAC TATGTTTTTA    4560
TGTTTATTAC ATATCAACTA GCACCTAGAA AATTATATTA ATATACTTAC TATGTTTTTA    4620
TGTTTATTAC ATATTATTTT AAGATTAATT AAATTACAGC ATAGARATAT TGTACTTGTA    4680
TTTGATATAG GATTTAGAAG GTTTGTTATA TGGTATACAA TAACTGTAAG AAATAGAAGA    4740
ACATTTAGAT CATAGTTAGT AGTTTGTTTT ATAAAATGTA TTGTAAACCA TTAATGTATG    4800
TTGTTATGGT GTGGGTGGTT GGTTGGTTTG CCCTTAGAAT ATGTTAAGGA CCAAAAAAAA    4860
TCAATAAAAG ACATTTAAAA CTAAATGGCC TCGTATACTG TCTATAAGGT GAACTAACCT    4920
TACCATAAGT ATCAATCTGT CTTTAAGGGG GGGGTGGGTG GGAGATGCAC AACATCAGTA    4980
GACTGACTGG CCTGGTTGGT TGCTCTGCTT AATCAACCAG ACCGCGTAGC GGTCTGGTTG    5040
ATTAAGCGC                                                            5049
```

FIG.4D

```
             10         20         30         40         50         60
              |          |          |          |          |          |
vB1440   ATCATTCTTTAGAACCAACTGACCAAGTTCACGTACGTATGACGTGATGACGCGCGTAC
CPV Y1   -----------------------------------------------------------G-
CPV-D    -----------------------------------------------------------G-
CPV-N    --------------------------------------------------C-- --G-
FPV-b    -----------------------------------------------------------G-
MVP      ------ --------TG--CA----T---------A--  -----------------T-
MVM1     --- ---------TG--CA----T---------A--   -----------------T-
MVPp     --- ---------TG--CA----T---------A--   -----------------G-
H1       ---- --------TG--CA----T-------C-A--    -----------------G-
PPV      -A------ ---TG--CA TGTC--TG----T- G---------------------

70         80         90        100        110        120
              |          |          |          |          |          |
vB1440   GCGCGCTGCCTACGGCAGTCACACGTCATACGTACGTTCCTTGGTCAGTTGGTTCTAAAG
CPV Y1   --------------------------------C---------------------------
CPV-265  --------------------------------C---------------------------
CPV-N    --------------------------------C---------------------------
FPV-b    --------------------------------C---------------------------
MVP      -----------G----------------CTTACGTC-CA-A----TG--CA--------
MVM1     -----------T---AC-----------CTTACGTT-CA-A----TG--CA--------
MVMp     ------ ----T---AC-----------CTTACGTT-CA-A----TG--CA--------
H1       -----------T----------------CTA-CGTT-CA-A----TG--CA--------
PPV      -----------T----------------CCATC-GCAAAGACA--TG--CA--- -----

130        140        150        160        170        180
              |          |          |          |          |          |
vB1440   AATGATAGGCGGTTT GTGTGTTT AAACTTGGGCGGGAAAAGGTGGCGGGC TAATTGT
CPV Y1   ------------------------------------------------------------
CPV-265  ------------------------------------------------------------
CPV-N    ------------------------------------------------------------
FPV-292  ------------------------------------------------------------
MVP      -------A------CA-A-A---- -G--CAA----C-------AA-T----G-GG--TA
MVM1     -------A------CA-A-A---- -G--CAA----C-------AA-T----G-GG--TA
MVMp     -------A------CA-G-A---- ----CAA----C-- -----AA-T----G-GG--TA
H1       -------A------CA-A-A----G----CAA---------C--AA-T----G-GGC-AA
PPV      -T-A---A-ACA--CCA-TG-C-GA--- GA---------TTCAAA AAAAGAGGCG-G
```

FIG.5

ATTENUATED CANINE PARVOVIRUS VACCINE

This application is a continuation-in-part of application Ser. No. 08/336,345, filed Nov. 8, 1994, now U.S. Pat. No. 5,814,510 which is incorporated by reference herein in its entirety.

1. INTRODUCTION

The invention is directed to novel attenuated canine parvovirus (CPV) strains which may be used as veterinary vaccines against CPV disease and other related veterinary viral diseases. The invention is further directed to a virus stock generated from a genomic DNA clone of such attenuated CPV virus strains for use as veterinary vaccines, and methods for vaccine production.

2. BACKGROUND OF THE INVENTION

During 1978 and 1979, outbreaks of previously unrecognized disease were observed in dogs in a number of countries. Identification of the causative agent, canine parvovirus (CPV), was made when comparisons between the disease seen in dogs and those caused in cats by feline panleukopenia virus (FPV) or in minks by mink enteritis virus (MEV), both parvoviruses, were noted. CPV has become endemic in domestic and wild dog populations around the world. Rapid global spread of the virus was most likely due to the high viral titers found in feces of infected dogs (Parrish, C. R., Adv. Virus Res. 38:403–450, 1990).

Two clinical conditions are recognized—enteric disease in pups older than 4 to 5 weeks, and myocardial disease in pups 3 to 16 weeks old. CPV is responsible for serious illness and mortality in dogs, and pups less than 6 months old are particularly susceptible (Carmichael et al., Cornell Vet. 73:13–29, 1983).

Canine parvovirus (CPV) is an autonomous parvovirus with a DNA genome of about 5,000 bases of single-stranded DNA. Two structural genes are characterized (VP-1 and VP-2), as well as one or two non-structural (NS) genes (Parrish et al. J. Virol, 65:6544–6552, 1991).

The original strain of CPV (CPV-2), first identified in 1978, was almost completely replaced between 1979 and 1982 by an antigenic and genetic variant, CPV-2a. A later antigenic variant, CPV-2b, emerged around 1984 and became the predominant virus type by 1988. It has largely replaced the previous strains in the United States, such that over 90% of infected dogs now carry this strain. DNA sequence analysis shows that sequence variation in the VP1/VP2 genes gave rise to successive antigenic virus types, such that the CPV-2a strain differed in only 5 or 6 amino acids from CPV-2, while CPV-2b differs in only 2 amino acids from CPV-2a (Parrish et al. J. Virol 65:6544–6552, 1991).

Vaccines designed to elicit protection against previous strains of CPV have been developed, including live (U.S. Pat. No. 4,303,645 dated Dec. 1, 1981; U.S. Pat. No. 4,810,494 dated Mar. 7, 1989) inactivated (U.S. Pat. No. 4,193,991 dated Mar. 18, 1980), heterotypic (U.S. Pat. No. 4,193,990 dated Mar. 18, 1980) as well as recombinant subunit vaccines (U.S. Pat. No. 4,971,793 dated Nov. 20, 1990; Lopez de Turiso et al., J. Virol. 66:2748–2753, 1992). Baculovirus expression of the CPV capsid genes generated empty parvoviral capsids which could be used to immunize dogs against challenge with CPV-2b (Mazzara et al., Vaccines' 87, Cold Spring Harbor Laboratory Press, 1987, p. 419–424; Saliki et al., J. Gen. Virol. 73:369–374, 1992).

The advantage of a vaccine derived from an attenuated virus over a heterotypic, inactivated, or recombinant vaccine is that the virus is able to reproduce in the host system such that an immune response is maintained over time.

Until the invention described herein, no attenuated vaccines have been developed which are derived from the most recent CPV-2b strain that is the most prevalent form of the virus found in infected dogs.

Citation or identification of any of the references in Section 2 of this application shall not be construed as an admission that such reference is available as prior art to the present invention.

3. SUMMARY OF THE INVENTION

It is an object of the present invention to provide attenuated canine parvoviruses derived from serial passaging of a virulent CPV-2b isolate. Such viruses are provided herein, the DNA of which differs in nucleotide sequence from that of wild-type CPV-2b. The DNA from the attenuated strains is used for the production of infectious molecular DNA clones, which, in turn, can be transfected into cells to generate stable master stocks of the virus. The attenuated viruses can be used in dogs as a vaccine for the prevention of CPV disease. In a preferred embodiment, the attenuated virus vBI440 (ATCC Accession No. VR 2489) or CPV-39 passage 65 (ATCC Accession No. VR 2528) is used as the vaccine. The present invention may be understood more fully by reference to the detailed description and illustrative examples which are intended to exemplify non-limiting embodiments of the invention.

4. DESCRIPTION OF THE FIGURES

FIG. 1. FIG. 1 represents a schematic diagram of the full-length CPV genome and the subcloned fragments of the genome which were ligated to form a continuous fragment that was cloned into plasmid pGEM5Z.

Figure 2A:
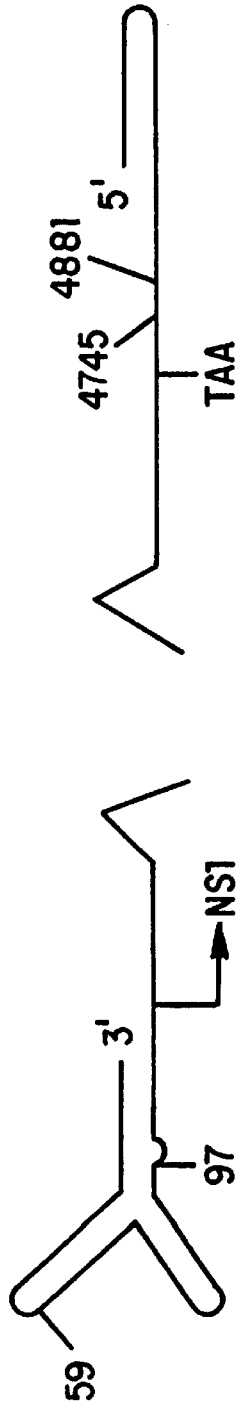
Figure 2B:
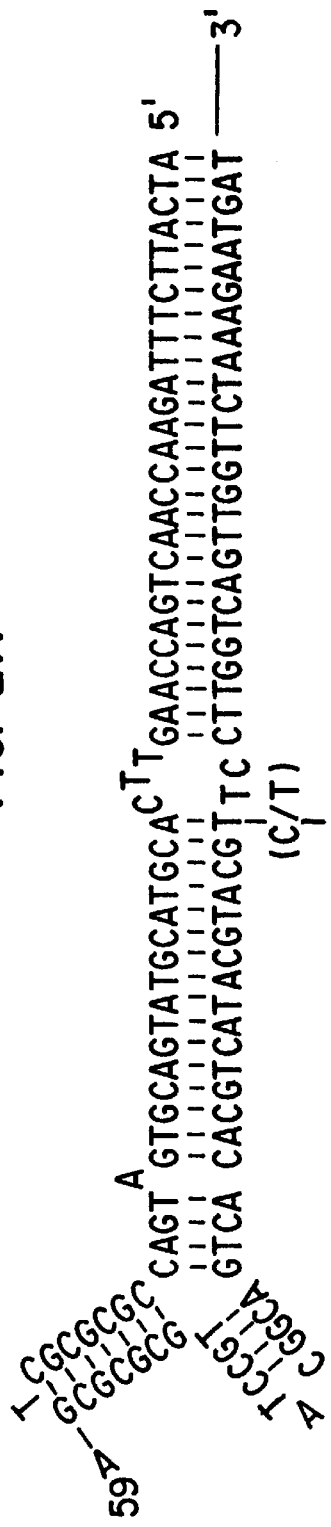
Figure 2C:
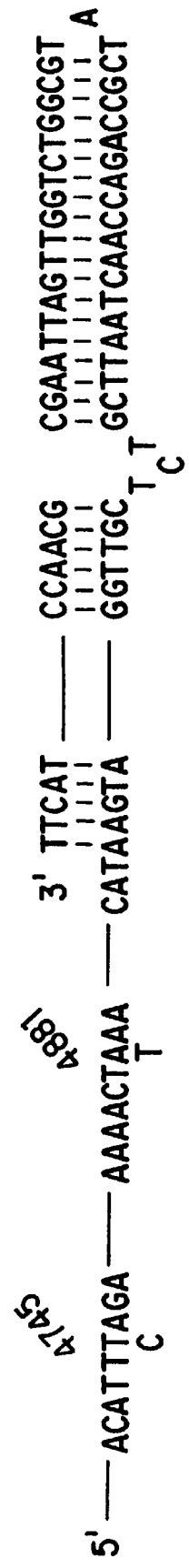

FIGS. 2A–2C. FIG. 2A represents a schematic diagram of the positions of the sequence changes detected in pBI440 relative to the control genome of the #5 passage, showing the 5' and 3' changes relative to coding regions and secondary structures in the CPV genome. FIG. 2B shows the location of the sequence differences in the 3' terminal hairpins. The sequence shown is the (+) strand, which is complementary to the (−) strand, the latter being the strand most commonly found in the virion. FIG. 2C shows the location of sequence differences in the 60th passage infectious clone which differ from the 5th passage sequence; the (+) strand is shown.

FIG. 3. FIGS. 3A–3E represent the DNA sequence of CPV-39 passage #60 which was cloned into pBI440.

FIG. 4. FIGS. 4A–4D represent the DNA sequence of CPV-39 passage #5.

FIG. 5. FIG. 5 shows an alignment of the 3'-terminal sequences of several parvoviruses, showing the conservation of the sequences, and the areas of sequence diversity. The two differences associated with the attenuated virus in this region, nucleotides 59 and 97, are marked. Sequences include vBI440, described herein, as well as others obtained from GenBank, for which the accession numbers are listed. CPV-d (CPV-type 2) (M38245); CPV-N (CPV-type 2) (M19296); FPV-b (M38246); CPV-Y1 (CPV-type 2a) (D26079); PPV (NADL-2) (L23427); MVMi (M12032); MVMp (M14704); and H1 (J02198).

5. DETAILED DESCRIPTION OF THE INVENTION

In one embodiment of the invention, novel attenuated strains of canine parvovirus useful as veterinary vaccines against CPV disease have been isolated. Infectious molecular DNA clones based on the genome of the attenuated strains have been produced and may be used to generate stable master stocks of each attenuated CPV strain.

5.1. Isolation of Attenuated Canine Parvovirus

This embodiment of the present invention is directed to the isolation of attenuated strains of canine parvovirus to be used as vaccines to protect animals, such as wild or domestic dogs, against CPV. It is further contemplated that such vaccines will be useful for protecting other animals, such as cats or minks, against diseases caused by viruses that are antigenically related to CPV, such as Feline Panleukopenia Virus (FPV) or mink enteritis virus.

Attenuation of a virulent isolate of CPV is achieved by serial passaging of such virus in a suitable host cell line (see e.g., Carmichael et al., Cornell Vet. 71:408–471, 1981) over time so that mutations accumulate that confer attenuation on the isolate. Serial passaging refers to the infection of a cell line with a virus isolate, the recovery of the viral progeny from the host cells, and the subsequent infection of host cells with the viral progeny to generate the next passage. Cell lines for the passaging of CPV include Norden Laboratory feline kidney (NLFK), mink lung cells, Madin-Darby canine kidney cells, canine A72 cells, and Crandell feline kidney (CRFK) cells.

Virulent CPV may be recovered from the feces of infected dogs and subsequently grown in tissue culture cells (Appel et al., Vet. Rec. 105:156–159, 1979). Isolation of CPV may be performed by disruption of infected cells with sonication or cycles of freezing and thawing followed by virus purification (Parrish, Virology 183:195–205, 1991).

CPV isolates which may be used to develop an attenuated strain that is protective against CPV-2b include, but is not limited to, CPV-39 as well as other isolates known to those skilled in the art (Parrish et al., J. Virol. 65:6544–6552, 1991).

Serial passaging of a virulent (disease-causing) strain of CPV results in the isolation of variants which are attenuated, i.e., infectious, yet not capable of causing disease. These attenuated variants are identified through testing of a passaged isolate on a suitable subject population, i.e., dogs, so that the clinical profile of the infected subjects can be ascertained. When a passaged virus is identified that infects dogs, yet is incapable of causing disease or causing only mild symptoms, it is characterized as attenuated. This passaged virus is then further characterized for its ability to serve as a vaccine against CPV disease, i.e., to confer protective immunity against challenge with virulent CPV or other viruses antigenically related to CPV.

In one embodiment of the invention, a virulent CPV-2b isolate was serially passaged in NLFK cells to derive the attenuated strains. Serial passaging was performed by infecting NLFK cells with the virulent strain, incubating the infected cells for several days, collecting and then freezing and thawing the infected cells to release virus. An inoculum from the previous passage was then applied to fresh, thinly seeded NLFK cells to generate the next passage. Each passage was similarly performed and collected. Hemagglutination (HA) assay of selected passages was used to identify the endpoint dilution of virus, and this dilution was used to generate the next passage.

In an embodiment of the invention described, infra, various passages in the series were tested for clinical effect. Dogs from 8–35 weeks of age were inoculated with passaged virus, either by oro-nasal or subcutaneous routes. The virulence of a passaged virus, i.e., the ability to cause disease, was assessed by daily monitoring of reduced appetite, malaise, elevated temperature, vomiting/diarrhea, lymphopenia, weight loss and fecal shed in the infected dogs. Virulence was retained up to the 15th passage, while attenuation was observed at subsequent passages. The 60th passage was attenuated, as judged by the inability of this virus to elicit clinical signs of CPV disease (Table 1, infra) (Abstract presented at the Fifth Parvovirus Workshop, Crystal River, Fla., Nov. 10–14, 1993.) Serial backpassages of this strain in dogs did not cause reversion to virulence.

Further passaging was performed on the 60th passage strain. The 65th passage was examined and was also found to be attenuated (Table I, infra). Moreover, five serial backpassages of passage #65 were performed in dogs without reversion to virulence.

5.2. Construction of an Infectious CPV Clone from an Attenuated Strain and the Generation of an Attenuated Stock The DNA genome of autonomous parvoviruses is able to initiate a productive infection when introduced into host cells by transfection. The infectious DNA genome of an attenuated virus is engineered into a vector for introduction into host cells for the production of progeny virus which are genetically identical to the parent attenuated isolate. The vector may be engineered to carry the viral genome using standard in vitro recombinant DNA techniques known to those skilled in the art (Ausubel et al., Current Protocols in Molecular Biology, Greene Publishing Associates & Wiley Interscience, New York, 1989). Vectors which may be used to deliver the genome into host cells include pGEM3Z, pGEM5Z (Promega Corporation, Madison, Wis.), and other similar plasmid vectors. Stable master stocks of a virus with desirable characteristics, i.e., attenuation, may be generated.

The ability to generate viral progeny through plasmid-mediated introduction of a viral genome can also be used to produce viruses with defined molecular changes. In this embodiment of the invention, stable virus stocks can be produced that contain altered DNA sequences that confer desired properties on the virus, for example, reduced virulence. This approach can also be used to assess the effect of molecular changes on various properties of the virus, e.g., antigenic type, virulence, or attenuation by introducing desired sequence changes into the viral genome, producing virus progeny from the genome, and recovering the virus progeny for characterization. In addition, this approach can be used to construct a virus with heterologous sequences inserted into the viral genome that are concurrently delivered by the virus to generate an immune response against other disease-causing viruses or agents, such as bacteria. Such viruses or agents include, but are not limited to, canine adenovirus, canine distemper virus, canine corona virus, feline panleukopenia virus and Leptospira.

Construction of viral genomes with defined molecular changes can be accomplished using standard techniques such as oligonucleotide-directed, linker-scanning or polymerase chain reaction-based mutagenesis techniques known to those skilled in the art (Zoller and Smith DNA 3:479–488, 1984; Botstein and Shortle Science 229:1193, 1985; Ausubel et al., Current Protocols in Molecular Biology, Greene Publishing Associates & Wiley Interscience, New York, 1989, Chapter 8). Ligation of the genome into a suitable vector for transfer may be accomplished through standard techniques known to those skilled in the art. Transfection of the vector into host cells for the production of viral progeny may be done using any of the standard techniques such as calcium-phosphate or DEAE-dextran mediated transfection, electroporation, protoplast fusion, and other techniques known to those skilled in the art (Sambrook et al., Molecular Cloning: A Laboratory Manual, Cold Spring Harbor Laboratory Press, 1989).

In one embodiment of the present invention, viral DNA was prepared from the attenuated strain derived from the 60th passage of CPV-2b and cloned into a plasmid for transfer into host cells by transfection. Progeny virus was produced and recovered from the transfected cells. The resulting virus stock (vBI440) was confirmed as an attenuated strain. This virus was used as a vaccine against virulent CPV-2b. In a similar manner, the DNA of the other attenuated viral strains described herein may be cloned into plasmids for further propagation and vaccine production.

5.3. Sequence of Attenuated Canine Parvovirus

The isolation of an attenuated virus may be followed by a sequence analysis of its genome to determine the basis for the attenuated phenotype. This is accomplished by sequencing the viral DNA and identifying nucleotide changes in the attenuated isolate relative to the genomic sequence of a control virus. Therefore, the molecular changes that confer attenuation on a virulent strain can be characterized.

In an embodiment of the invention, the sequence of the DNA genome isolated from the attenuated virus (60th passage) was determined and compared to a control genome (5th passage). Nucleotide sequence variations between the virulent strain and the attenuated strain were identified. Three or four nucleotide alterations were found in the attenuated virus genome, in the 5' and 3' nontranslated regions (Table 2 and Table 2A, infra).

The invention provides for attenuated CPV-2b viruses which have one or more of the following sequence alterations relative to the sequence of the control (5th passage) wild-type CPV-2b (SEQ. ID NO. 2):

nucleotide at position 59 A or C or T
nucleotide at position 97 A or G or T
nucleotide at position 4745 A or C or G
nucleotide at position 4881 A or G or T In one embodiment of the invention provided herein, the viral genome with alterations at all 4 positions (SEQ. ID. NO. 1) relative to the wild-type sequence was used to produce an attenuated virus stock. Other embodiments include the introduction of sequence changes at 1, 2 or 3 of the sites noted above in order to generate attenuated virus progeny. Viral genomes with such alterations can be produced by any of the techniques described in Section 5.2, supra, for the introduction of nucleotide changes into cloned DNA. A genome may then be ligated into an appropriate vector for transfection into host cells (Section 5.2, supra) for the production of viral progeny.

The invention also provides for attenuated CPV-2b viruses which have one or more of the following sequence alterations relative to the sequence of the control (5th passage) wild-type CPV-2b (SEQ. ID NO. 2):

nucleotide at position 4307 C or G or T
nucleotide at position 4358 A or G or T
nucleotide at position 4409 A or G or T
nucleotide at position 4477 A or C or T
nucleotide at position 4889 A or G or T
nucleotide at position 4973 A or G or T In one embodiment of the invention provided herein, an attenuated virus with alterations at all 6 positions relative to the wild-type sequence was isolated. In another embodiment of the invention provided herein, the viral genome with alterations at all 6 positions relative to the wild-type is used to produce an attenuated virus stock. Other embodiments include the introduction of sequence changes at 1, 2, 3, 4, or 5 of the sites noted above in order to generate attenuated virus progeny. Viral genomes with such alterations can be produced by any of the techniques described in Section 5.2, supra, for the introduction of nucleotide changes into cloned DNA. A genome may then be ligated into an appropriate vector for transfection into host cells (Section 5.2, supra) for the production of viral progeny.

The present invention encompasses all possible variations of identified sequence variations of the attenuated viruses. For example, and not by way of any limitation, the 10 nucleotide changes present, collectively, in passage 60 and passage 65 virus as compared to passage 5 may all be present, or any permutation of any subset of these nucleotide changes may be present, in an attenuated virus, e.g., an attenuated strain may contain sequence differences, as compared to passage 5, at nucleotide positions #59, #97, #4745 and #4881, or may contain sequence differences at positions #59, #97, and #4973, or at positions #4307, #4358, #4409, #4477, #4889, and #4973, or at positions #59 and #4307.

The present invention also encompasses the production of attenuated virus through recombination or genetic engineering of viral nucleic acid sequences. For example, the recombination of attenuated virus with wild type (non-attenuated) virus by methods known to those of skill in the art (Sambrook et al., 1990, Molecular Cloning, A Laboratory Manual, 2nd ed., Cold Spring Harbor Laboratory, Cold Spring Harbor, N.Y.). The recombinants may then be screened for attenuation in animal models, for example, in dogs (Section 10, infra). Additionally, non-attenuated viral DNA sequences may also be modified by site-directed mutagenesis at selected nucleotide positions, (Hutchinson, et al., 1978, J. Biol. Chem. 253:6551), and subsequently screened for attenuation.

Additionally, the viral nucleic acid sequence may be mutated in vitro or in vivo, to create and/or destroy translation, initiation, and/or termination sequences, or to create variations in coding and/or non-coding regions and/or form new restriction endonuclease sites or destroy existing ones, to facilitate further in vitro modification. Any technique for mutagenesis known in the art may be used, including but not limited to, in vitro site-directed mutagenesis (Hutchinson, et al., 1978, J. Biol. Chem. 253:6551).

5.4. Attenuated Canine Parvovirus as a Vaccine

The invention may be used as a vaccine to protect dogs from disease resulting from challenge with all extant strains of CPV, types 2, 2a and 2b. The vaccine may be an attenuated virus isolate, or, alternatively, the vaccine may be comprised of virus which has been generated from an infectious genomic clone of an attenuated virus.

Preparation of the vaccine may be accomplished by growing large-scale stocks of the attenuated virus in tissue culture. Alternatively, the plasmid which contains the genome of the attenuated virus may be transfected into host cells to generate large-scale virus stock. The viruses may be recovered from host cells by disruption by, for example, sonication or cycles of freezing and thawing (Parrish, Virology 183:195–205, 1991).

Determination of virus yield may be performed with the use of a hemagglutination assay (Carmichael et al., Am. J. Vet. Res. 41: 784–791, 1980) or plaque assay (Chang et al., J. Virol. 66:6858–6867, 1988).

The vaccine may be comprised of an inoculum which is an aliquot from an attenuated virus stock. The vaccine may be prepared as a suspension or, alternatively, the vaccine may be lyophilized. The attenuated virus may be suspended in a pharmaceutically acceptable carrier, including but not limited to, phosphate-buffered saline.

The attenuated virus may be combined with other ingredients and antigens for the production of a vaccine. The attenuated virus may be given in combination with other antigens, including, but not limited to, canine adenovirus, canine distemper virus, canine coronavirus, or Leptospira antigens to form a combination vaccine. Stabilizers may be added to such a vaccine, including but not limited to, gelatin, sorbitol, mannitol, glucose, sucrose, dextran, albumin, SPGA (Bovarnick, J. Bact. 59:509, 1950) or others known to those skilled in the art.

Subject populations for evaluation of a candidate vaccine include wild and domestic dogs and wild and domestic cats.

Dosage of the vaccine may range from about $10^2$ to about $10^7$ tissue culture infectious dose$_{50}$ (TCID$_{50}$). A dosage greater than $10^7$ TCID$_{50}$ may be given. In a preferred embodiment, the dosage is $10^5$ TCID$_{50}$. A minimal immunizing dose (MID) may be determined by vaccinating a subject population with graded 10-fold dilutions of an attenuated virus stock, and assaying the animals for HI titer (Carmichael et al., Cornell Vet. 73:13–29, 1983).

The vaccine may be administered by several parenteral routes, including subcutaneously, intramuscularly, or intravenously. The vaccine may also be administered by oral or nasal routes. Repeated administration may be given, including but not limited to, yearly booster shots.

The safety of the vaccine can be determined by the absence of adverse effects, i.e., evidence of illness generated by the administration of the vaccine in a test population prior to challenge with virulent virus.

The immune response generated by the vaccine can be assayed by testing sera from inoculated dogs using hemagglutination-inhibition (HI) titers (Carmichael et al., Am. J. Vet. Res. 41: 784–791, 1980). The development of antibodies to the attenuated virus correlates with an increase in HI titer, and the generation of this protective response is defined as vaccination. Protection can be correlated with the development of an HI titer that exceeds 1:40.

The efficacy of the vaccine can be determined by the ability of the vaccine to confer resistance on a subject population when challenged with virulent CPV. Challenge may performed when an interval has elapsed after vaccination, for example, from 14–20 days. Duration of immunity afforded by the vaccine may be determined by periodic assessment of HI titers in vaccinated animals or by challenge with virulent CPV and observation of clinical signs of CPV disease.

In one embodiment of the invention, virus derived from the infectious molecular clone of the attenuated strain (vBI440) was used to vaccinate pups (Section 10, infra). After challenge with virulent CPV, the vaccinated dogs did not evidence signs of disease. Hemagglutination-inhibition (HI) titers of the vaccinated animals showed the development of a serological response to the attenuated virus vaccine.

6. EXAMPLE: ISOLATION OF ATTENUATED CANINE PARVOVIRUS STRAIN

6.1. Methods

To produce a virus strain capable of eliciting protection against virulent CPV-2b, a CPV-2b isolate (CPV-39, a 1984 CPV isolate from a dog with diarrhea) was obtained from the Texas Veterinary Medical Diagnostic Laboratory (accession number C84176071, No. 2). This isolate was confirmed as a CPV-2b isolate by typing against a panel of monoclonal antibodies (Parrish et al., J. Virol. 65:6544–6552, 1991). The virus was originally passaged five times in NLFK cells to establish a stock virus preparation.

The NLFK feline kidney host cells (a derivative of the Crandell cell line, Crandell et al., 1973, In Vitro 9:176–185) used in these experiments were grown in a mixture of 50% McCoy's 5a and 50% Leibovitz L15 media with 5% fetal bovine serum at 370° C.

CPV-39 was serially passaged in NLFK cells. Serial passaging was performed by infecting NLFK cells with CPV-39, incubating the infected cells for between 5–7 days, and then freezing and thawing the infected cells to release viral progeny. Virus from the cell lysate (1–2 ml) was then applied to fresh, thinly seeded NLFK cells to generate the subsequent passage in the series. Each passage was similarly performed and collected.

At various passages (passage 3, 15, 20, 25, 35, 44, 50 and 60) the virus-containing materials were diluted in a 10-fold series in tissue culture medium, and the dilutions inoculated onto thinly seeded NLFK cells. After incubation for 4–5 days, the cultures were frozen and thawed, and the medium tested for virus hemagglutination of rhesus macaque erythrocytes (HA assay). The subsequent passage in each case was made using the culture inoculated with the endpoint dilution of the virus as determined in the HA assay.

The HA assay was performed in a microtiter plate by incubating 0.025 ml of a virus dilution per well with 0.025 ml of barbitol-buffered saline (BBS) to which is added 0.050 ml of a 0.5% v/v suspension of rhesus erythrocytes in BBS/bovine serum albumin (BSA). The plate was shaken to mix and placed at 4° C. for the cells to settle. The HA titer is read as the last well containing >50% agglutinated cells.

Various passages (passage 3, 15, 20, 25, 35, 44, 50, 60 and 65) in the series were tested for the ability to induce disease in dogs. In each test between 2 and 5 specific-pathogen-free (SPF) beagle dogs, aged between 8–35 weeks, were inoculated with $10^{5.5}$ to $10^{6.2}$ tissue culture infectious dose-50 (TCID$_{50}$) units of passaged virus, either by oro-nasal (ON) or subcutaneous (SC) routes. Virulence was judged by looking for clinical signs typical of CPV infection, including reduced appetite, malaise, elevated temperature, weight loss, pyrexia, depression, anorexia, diarrhea and vomiting, while attenuation was judged by the reduction or absence of these symptoms within 10 days post-infection (Carmen and Povey, 1985, Res. Vet. Sci. 38:134–140; Carmichael et al., 1981, Cornell Vet. 71:408–427; Macartney et al., 1984, Vet. Rec. 115: 201–210; Meurnier et al., 1985, Vet. Pathol. 22:617–324; Pollock, 1982, Cornell Vet. 72:103–119). Severe disease was not observed in these specific pathogen free dogs with any of the viruses tested, and all studies were conducted in accordance with all applicable animal care and use regulations.

6.2. Results

Virulence was retained up to the 15th passage (#15), was greatly reduced by the 20th passage (#20), while the 60th passage (#60) and the 65th (#65) caused no clinical symptoms in susceptible puppies (Table 1), and were characterized as attenuated. Non-inoculated control dogs remained clinically normal.

7. EXAMPLE: PRODUCTION OF VIRUS FROM MOLECULAR CLONE OF ATTENUATED STRAIN

7.1. Methods

Stock virus was prepared from the 5th, 60th, and 65th passages by infecting thinly seeded NLFK cells, culturing the virus-infected cells for 36 hours, lysing the cells and the viral replicative form (RF) DNA (double-stranded) was recovered using a modification of the Hirt procedure for the isolation of low molecular weight DNA (Parrish et al., Amer. J. Vet. Res. 45:2591–2599, 1984; Parrish and Carmichael, 1986, Virology 148:121–132). The recovered DNA was purified by preparative agarose gel electrophoresis (Ausubel et al., Current Protocols in Molecular Biology, Greene Publishing Associates & Wiley Interscience, New York, 1989), and the viral RF DNA was recovered from the gel by electroelution (Ausubel et al., supra).

The cloning strategies used are outlined in FIG. 1. The left hand terminus of the RF DNA from the 60th passage virus was repaired by incubating with *Escherichia coli* DNA polymerase I (Klenow fragment) and dNTPs, then the DNA was digested with EcoRI. The resulting 1100 nucleotides (nts.) left hand terminal fragment was purified and cloned into the plasmid vector pGEM3Z (Promega, Madison, Wis.) digested with EcoRI and HincII.

The right hand terminus of the 60th passage virus was cloned after viral RF DNA was digested with HinpI and the region between nts. 4294 and 5045 was ligated into pGEM3Z digested with AccI (FIG. 1). After digesting that clone with EcoRI (in the plasmid polylinker) and PacI (nucleotide (nt.) 4650), the isolated fragment was ligated to 35 an EcoRI-PacI DNA fragment isolated from viral RF DNA, giving a plasmid containing the viral sequence from nts. 1100 to 5045 (FIG. 1). The two cloned fragments prepared by digestion with EcoRI and PstI or SphI were then assembled into pGEM5Z digested with PstI and SphI, to give the full length plasmid clone (pBI440). This infectious plasmid clone included sequences from nt. 1 to 5045 of the complete CPV genome, ending about 75 bases short of the common 5' end of the virus genome.

The left hand genomic terminus of the 5th passage viruses was cloned from RF DNA as described above. For the 5th passage virus, fragments between EcoRI (21 map units) and EcoRV (77 map units) and between the HaeIII sites at 74 and 95 map units have been previously prepared and their capsid protein gene sequences reported (Parrish et al., 1991, J. Virol. 65:6544–6552).

The right hand terminus of the 5th passage virus was cloned after viral RF DNA was digested with HinpI and the region between nts. 4294 and 5045 was ligated into pGEM3Z digested with AccI (FIG. 1). After digesting that clone with EcoRI (in the plasmid polylinker) and PacI (nt. 4650), the isolated fragment was ligated to an EcoRI-PacI DNA fragment isolated from viral RF DNA, giving a plasmid containing the viral sequence from nts. 1100 to 5045 (FIG. 1). The two cloned fragments prepared by digestion with EcoRI and PstI or SphI were then assembled into pGEM5Z digested with PstI and SphI.

The left hand genomic terminus of the 65th passage viruses was cloned from RF DNA as described above. For the 65th passage virus, fragments between EcoRI (21 map units) and EcoRV (77 map units) and between the HaeIII sites at 74 and 95 map units have been previously prepared and their capsid protein gene sequences reported (Parrish et al., 1991, J. Virol. 65:6544–6552). The right hand genomic terminus of the 65th passage viruses was cloned in accordance with the same strategy described above for the 5th passage viruses, i.e., using a HinpI digestion of viral RF DNA and inserting the region between nts. 4294 and 5045 into an AccI-digested pGEM3Z vector, followed by ligation.

Plasmid DNAs were banded in CsCl gradients, then 10 $\mu$g of plasmid pGEM5Z was electroporated into NLFK cells (at 220 V/330 uF) to initiate a virus infection from the genome. Virus generated by the transfection of the infectious genomic clone was recovered from the NLFK cells by freezing and thawing. The virus was passaged three times. The resulting virus (vBI440) was tested against a panel of type-specific monoclonal antibodies by hemagglutination-inhibition (HI) assay (see Section 10, infra) and the derivation of this virus from the original CPV-39 was confirmed (Parrish et al., J. Virol. 65: 6544–6552, 1991).

Eight 9 week-old beagle pups were inoculated subcutaneously with $10^5$ tissue culture infectious dose-50 ($TCID_{50}$) units of the vBI440 strain to determine if the attenuated phenotype of the parent virus (#60 passage) was retained. The dogs were monitored at daily intervals and virus extracted from the feces of the first passage dogs was inoculated three further times sequentially into pairs of SPF beagle pups, the feces in each case being collected and the virus recovered used to inoculate dogs in the next passage.

Also, four 6–8 week-old beagle pups were inoculated subcutaneously with $10^{6.2}$ tissue culture infectious dose-50 ($TCID_{50}$) units of the plaque cloned passage #65 virus to determine if the passage #65 virus also has the attenuated phenotype of the #60 passage. The dogs were monitored at daily intervals and virus extracted from the feces of the first passage dogs was inoculated four further times sequentially into pairs of SPF beagle pups, the feces in each case being collected and the virus recovered used to inoculate dogs in the next passage.

7.2. Results

Clinical analysis of the pups inoculated with vBI440 (#60-cloned strain) and passage #65 revealed that these viruses did not cause any signs of CPV disease (Table 1), as judged by the absence of CPV-like symptoms, and therefore could be characterized as attenuated. Serial backpassages of these strains in dogs did not cause illness.

The virus derived from passage #60 in the series was passaged for another 15 passages in NLFK cells, at which time a non-hemagglutinating variant emerged. By the 75th passage the original line of virus lost the ability to hemagglutinate (HA) rhesus macaque erythrocytes, although that virus still provoked normal antibody responses in dogs. In contrast, 15 passages of vBI440 in NLFK cells showed no apparent phenotypic variation, illustrating the stability of the virus derived from the genome of the attenuated strain.

The virus derived from the plasmid had the antigenic type of CPV type-2b, and it did not cause disease in dogs during 4 sequential passages in dogs, indicating that the attenuation was a stable property.

TABLE 1

Clinical Responses of Pups Inoculated by the Oral-Nasal (On) or Subcutaneous (Sc) Route with Different Passage Levels of CPV-2b and Infectious Clone of Passage #60

| Virus Passage | No. Dogs/age/ Route Inoc. | Reduced Appetite | Malaise | Elevated Temp[1] | Vomiting/ Diarrhea | Lympho-penia[2] | Weight Loss[3] | Fecal Shed[4] |
|---|---|---|---|---|---|---|---|---|
| #3 | 5/20 wk/ON | 5/5 | 5/5 | 4/5 | 5/5 | 5/5 | 5/5 | 5/5 |
| #15 | 3/17 wk/ON | 2/3 | 0/3 | 1/3 | 0/3 | 3/3 | 3/3 | 3/3 |
| #20 | 2/16 wk/ON | 0/2 | 0/2 | 1/2 | 0/2 | 2/2 | 0/2 | 2/2 |
| #25 | 2/8 wk/SC | 0/2 | 0/2 | 1/2 | 0/2 | 2/2 | 0/2 | 2/2 |
| " | 2/8 wk/ON | 1/2 | 0/2 | 2/2 | 0/2 | 2/2 | 0/2 | 2/2 |

TABLE 1-continued

Clinical Responses of Pups Inoculated by the Oral-Nasal (On) or Subcutaneous (Sc) Route with
Different Passage Levels of CPV-2b and Infectious Clone of Passage #60

| Virus Passage | No. Dogs/age/ Route Inoc. | Reduced Appetite | Malaise | Elevated Temp[1] | Vomiting/ Diarrhea | Lympho- penia[2] | Weight Loss[3] | Fecal Shed[4] |
|---|---|---|---|---|---|---|---|---|
| #35 | 2/10 wk/SC | 1/2 | 1/2 | 1/2 | 1/2 | 2/2 | 2/2 | 2/2 |
| #44 | 5/35 wk/SC | 0/5 | 0/5 | 4/5 | 0/5 | Not Done | 0/5 | 5/5 |
| #50 | 2/8 wk/ON | 0/2 | 0/2 | 0/2 | 0/2 | 2/2 | 0/2 | 2/2 |
| " | 2/8 wk/SC | 0/2 | 0/2 | 0/2 | 0/2 | 2/2 | 0/2 | 2/2 |
| #60 | 5/8 wk/SC | 0/5 | 0/5 | 0/5 | 0/5 | 2/5 (2 day) | 0/5 | 2/2 |
| #60 - cloned virus | 8/9 wk/SC | 0/8 | 0/8 | 1/8 (1 day) | 0/8 | 0/8 | 0/8 | 0/8 |
| #65 - cloned virus | 4/6–8 wk/SC | 0/4 | 0/4 | 0/4 | 0/4 | 0/4 | 0/4 | 0/4 |
| Recomb. 462[5] | 2/9 wk/ON | 0/2 | 0/2 | 0/2 | 0/2 | 0/2 | 0/2 | 2/2 |
| Recomb. 463[5] | 2/9 wk/ON | 0/2 | 0/2 | 0/2 | 0/2 | 2/2 | 0/2 | 2/2 |

[1]Number of dogs/total inoculated at this passage with temperature ≧103° F. (39.4° C.)
[2]Lymphopenia = lymphocyte counts <50% of pre-inoculation value. Total WBC counts done by Coulter counter. No dog had a panleukopenia.
[3]Weight loss = failure to gain normal weight or actual weight loss between time of infection and 2 weeks later.
[4]Fecal hemagglutination titer >2048 for at least 2 days.
[5]See Section 9, infra.

Attenuated variants of CPV type-2b have been isolated by repeated passage in feline cells in culture at 37° C. One attenuated virus, passage 60, replicated in dogs without causing disease, and efficiently induced antibody responses. The attenuated CPV type-2b derived strain, passage 60, differed antigenically from CPV type-2, which is the source of most of the current CPV vaccines (Parrish et al., 1991, Virology 183:195–205). In addition, CPV type-2a and type-2b virus strains contain sequence differences (VP2 residues 87, 300 and 305) in a region of their capsid structure which may affect canine and feline host ranges (Parrish and Carmichael, 1986, Virology 148:121–132; Truyen et al., 1994, Virology 200:494–503; Truyen et al.,1996, Virology 215:186–189).

The construction of an infectious DNA clone from the attenuated virus allows examination of the basis of attenuation, and also provides a defined and genetically stable plasmid clone for use as a molecular "master seed" for preparation of virus stocks and vaccines. The virus reisolated from the plasmid clone was attenuated, and on serial passage in dogs it did not show any reversion to virulence.

After further passages of the vBI440 virus in NLFK cells no phenotypic changes were observed. The loss of ability to HA erythrocytes of the uncloned virus was presumably through selection of a mutation such as has been defined in CPV type-2 (Barbis et al., 1991, Virology 191:301–308).

8. EXAMPLE: SEQUENCE ANALYSIS OF CLONED ATTENUATED VIRUS

8.1. Methods

Plasmid pBI440, containing the viral DNA of passage #60 cloned into pGEM5Z, was subcloned into M13 phage vectors mp18 and mp19 and the DNA was sequenced by the dideoxy method (Ausubel et al., Current Protocols in Molecular Biology, Greene Publishing Associates & Wiley Interscience, New York, 1989) using primers as described previously (Parrish et al., 1991, Virology 183:195–205). Sequencing was either from single stranded DNA prepared from M13 phage, or from plasmid DNA after alkali denaturation (Hattori and Sakaki, 1986). DNA prepared from the CPV-39 5th passage (#5) was also cloned into pGEM5Z and pGEM3Z and sequenced as a comparative control. The plasmid clone of 60th passage virus (pBI440) was sequenced completely from both DNA strands. Sequences of the 5th passage virus were mostly derived from both strands, although some regions were sequenced from only one DNA strand, with ambiguous sequences being confirmed from the opposite strand.

DNA prepared from the CPV-39 65th passage (#65) was cloned as described above in Section 7.1. A single clone from the 3' end, and four clones from the 5' end were sequenced.

8.2. Results

The sequence of the attenuated virus genome derived from passage #60 is given in FIGS. 3A–3E (SEQ. ID. NO. 1). The sequence of the control virus used for sequence comparison (passage #5) is given in FIG. 4 (SEQ. ID. NO. 2). Comparative differences between these genomes are shown in Table 2. The four differences between CPV-39 at the 5th and 60th passages were all located in the non-translated regions of the viral genome, two each near the 3' and 5' termini (FIG. 2A and 2B). The changes occurred at nucleotides #59, #97, #4745 and #4881.

The 3' changes were both within the hairpin formed by the 3' terminal palindrome (FIG. 2B). The change of nucleotide (nt.) #59 introduces an A into a G-C rich region within the tip of the hairpin, disrupting the base pairing in one of the two small internal palindromes within that sequence. The thymine at nt. 97 was adjacent to the mismatched bubble (flip-flop) sequence within the palindrome, and was also present in 4 of 6 DNA clones obtained for that region of the 5th passage virus.

The sequence differences near the 5' end of the genome of vBI440 were present in the non-coding region but before the terminal palindrome. The differences were not associated with the repeated sequences in that region.

Sequences of other clones derived from the 65th passage of the virus were also examined, and the 3' end sequence of a second clone was the same as vBI440, with changes of nts. 59 and 97. The sequence of the 5' end of the 65th passage virus differed from that of vBI440 as well as that of the 5th passage, in six places (Table 2). Specifically, the sequence of the 5' end of the 65th passage differed at nucleotides #4307, #4358, #4409, #4477, #4889 and #4973. The two changes present in vBI440 (4745 T-C; 4881 C-T) were not present, but the foregoing sequence differences within that region included three silent and one coding change within the VP1/VP2 gene. The coding difference was a predicted change of serine (Ser) to asparagine (Asn) of VP2 residue 564, a reversion to the feline panleukopenia virus (FPV) sequence (Parrish, 1991, Virology 183:195–205; Truyen et al., 1994, Virology 200:494–503).

TABLE 2

Nucleotide sequence differences between CPV-d, CPV-39 (passage 5), vBI440 (derived from 60th passage virus) and CPV-39 (passage 65, plaque cloned).

| nt/virus | CPV-d | CPV-39 P.5 | vBI440 | Passage 65 |
|---|---|---|---|---|
| 59 | G | G | A | A |
| 97 | C | C or T | T | T |
| 1649 | T | C | C | not determined |
| 1903 | A | T | T | not determined |
| 2198 | A | G | G | not determined |
| 3045 | A | T | T | not determined |
| 3088 | T | C | C | not determined |
| 3685 | C | G | G | not determined |
| 3699 | G | T | T | not determined |
| 3909 | A | G | G | not determined |
| 4062 | A | G | G | not determined |
| 4307 | A | A | A | G |
| 4358 | C | C | C | T |
| 4409 | C | C | C | A |
| 4477 | G | G | G | T |
| 4745 | T | T | C | T |
| 4779 | — | — | — | A |
| 4789 | T | C | C | C |
| 4853 | A | A | A | — |
| 4881 | C | C | T | C |
| 4889 | C | C | C | T |
| 4973 | C | C | C | T |
| 5026 | T | not determined | G | not determined |
| 5027 | A | not determined | T | not determined |
| 5028 | T | not determined | A | not determined |

Genome region are: nts. 1–272 3' noncoding region; 273–2279 NS1/NS2 coding region; 2286–4541 VP1/VP2 coding region; 4542–5058 5' noncoding region.

9. EXAMPLE: RECOMBINATION BETWEEN PASSAGE 5 AND PASSAGE 60

9.1 Methods

Only three or four nucleotide sequence differences were detected between the 5th passage and the plasmid cloned 60th passage virus, with one or two nucleotide sequence differences in the left hand terminal palindrome, and two in the right hand non-coding region of the genome. To attempt to determine which of those changes affected virulence, recombinant plasmids (pBI462 and pBI463) were prepared at the EcoRl site at nt. 1100, which contained the 0–21.3 map units (m.u.) region of the 5th passage and the 21.3–99 m.u. region of the attenuated plasmid clone (pBI440). Between $10^{4.5}$ and $10^5$ TCID$_{50}$ of each virus was inoculated into two 9-week old dogs and clinical signs examined, as described above.

9.2 Results

Inoculation of dogs with the recombinant viruses vBI462 (Recomb. 462) and vBI463 (Recomb. 463), which contained 3' end sequences of the wild type virus and the 5' end of vBI440, resulted in only mild clinical signs which were not as severe as those observed after inoculation of the 5th passage virus alone (Table 1).

Table 2A shows the nucleotide sequence differences at the left hand palindrome in the low passage CPV-d, CPV-39 (5th passage), and in two different recombinant mutant viruses containing nts. 1–1100 from CPV-39 (5th passage) (vBI462 and vBI463) and nts. 1101–5058 from pBI440 (60th passage).

TABLE 2A

| Virus | nt. 59 | nt. 97 |
|---|---|---|
| CPV-d | G | C |
| CPV-39 Passage 5 | G | C (n = 2) |
|  |  | T (n = 4) |
| vBI440 Passage 60 | A | T |
| vBI462 (Recomb. 462) | G | T |
| vBI463 (Recomb. 463) | G | C |

Analysis of recombinant plasmid clones based on pBI440 in which nt. 59 alone or nts. 59 and 97 were changed to those found in the virulent passage 5 virus showed that neither recombinant was virulent in dogs. This demonstrates that either the changes in the 5' non-coding region caused the attenuation, or changes from both ends of the genome were required together. As different sequences from those of vBI440 were found in the 5' end of the attenuated 65th passage plaque-cloned virus, it is likely that the latter explanation is possible.

10. EXAMPLE: VACCINATION WITH ATTENUATED vBI440

10.1. Methods

Five SPF 12.5 week-old beagle pups were vaccinated by the subcutaneous route with 1 dose ($10^5$ TCID$_{50}$/ml) of vBI440. Two control pups were kept in isolation until challenge with virulent CPV-39. Challenge was performed at 20 days after vaccination and consisted of inoculation with $10^{6.2}$ TCID$_{50}$ units in 3 ml of inoculum.

Pre-inoculation blood samples were taken for leukocyte counts and at intervals for 8 days post-challenge. Dogs were observed twice daily for signs of illness, including rectal temperatures. Fecal samples were also collected during the same time period and pooled samples from each isolation unit were prepared as a 10% volume suspension in phosphate-buffered saline and then tested for virulent viral shed using an HA assay.

Blood for serological testing was obtained on post-vaccination days 0, 7 and 21 and 10 days after challenge with virulent CPV-2b. Hemagglutination-inhibition (HI) titers of the vaccinated animals were performed by collecting animal sera and diluting 1:5 in BBS, then heat inactivating at 56° C. for 30 minutes. To the sera, 0.010 ml 50% packed red blood cells were added, and the mixture was allowed to stand for 1 hour at 4° C. In a microtiter well, 0.025 ml BBS, and serial dilutions of heat-inactivated sera, beginning at 0.025 ml, were added, followed by 0.025 ml of diluted antigen. Incubation of the plates for 1 hour at room temperature was followed by the addition of 0.050 ml 0.5% RBC suspension. An antigen control was set up by setting up a parallel plate without sera. All plates were shook and placed at 4° C for 4–16 hours. The HI titer is the reciprocal of the highest serum dilution that completely prevents hemagglutination.

10.2. Results

The vaccine, vBI440, did not cause symptoms of illness, as indicated by the normal temperature observed in vaccinated animals 1411–1415 (Table 3A, column days post-inoculation (DPI): −1, 0) as well as normal leukocyte values (Table 3A, column DPI: 0).

For 9 days following challenge with virulent CPV-39, all vaccinated animals (1411–1415) maintained normal temperature and normal blood values (WBC and Ly/PMN) (Table 3A, column DPI: 1–9). Fecal HA titers indicated no shed of virulent virus in the vaccinated animals. The vaccination with vBI440 offered protection against challenge with CPV-39, while non-vaccinated animals were susceptible to challenge.

In contrast, the non-vaccinated animals (1418, 1419) showed elevated temperatures by day 5 in the course of a 9-day period post-challenge, as well as a marked lymphopenia on days 4–7 (Table 3B, column Ly/PMN: 4–7) and leukopenia on day 6 (column WBC: 6). Fecal shed of virulent virus was observed on days 4 and 5, as determined from an HA assay.

The vaccine vBI440 elicited serological protection for the 5 vaccinated pups challenged with virulent CPV-39, as evidenced by the HI antibody titers in Table 4A. For vaccinated animals 1411–1415, HI titers had increased by 1 week post-vaccination relative to pre-inoculation levels (Table 4A, 1 wk. PI), further increasing by 3 weeks post-vaccination (Table 4A, 3 wk. PI), indicating that the antibodies to vBI440 had developed which afforded protection against the subsequent challenge with CPV-39. In contrast, in non-vaccinated animals 1418 and 1419, no significant HI titers were detected prior to challenge (Table 4B, prechallenge). Following challenge, non-vaccinated animals evidenced the development of antibodies to CPV after the course of disease had abated, as indicated by the increased HI titers observed at 10 and 21 days post-challenge (Table 4B).

TABLE 3

CLINICAL RESPONSES TO VACCINATION WITH vBI440 AND CHALLENGE WITH VIRULENT CPV-2b

A.

DOG NUMBER (v = vaccinated)

| DPI | 1411-V Temp WBC[1]/Ly/PMN | 1412-V Temp WBC/Ly/PMN | 1413-V Temp WBC/Ly/PMN | 1414-V Temp WBC/Ly/PMN | 1415-V Temp WBC/Ly/PMN |
|---|---|---|---|---|---|
| −1 | 102.0 . . . | 102.3 . . . | 102.5 . . . | 102.6 . . . | 102.3 . . . |
| 0 | 101.2 8.1/46/54 | 101.2 7.2./51/49 | 100.9 10.2/47/53 | 102.5 11.1/49/51 | 101.3 9.2/45/55 |
| 1 | 101.3 . . . | 101.8 . . . | 102.4 . . . | 101.8 . . . | 100.9 . . . |
| 2 | 102.4 9.0/40/60 | 102.5 8.0/46/54 | 101.7 9.2/44/56 | 100.8 10.7/45/55 | 102.2 10.0/50/50 |
| 3 | 102.0 7.7/39/61 | 102.4 7.6/40/60 | 102.0 9.9/49/51 | 102.8 9.7/47/53 | 101.8 9.5/39/51 |
| 4 | 102.2 . . . | 102.4 | 102.1 . . . | 102.4 . . . | 102.0 . . . |
| 5 | 102.3 8.7/47/53 | 101.9 7.9/36/64 | 101.3 11.3/35/65 | 102.7 10.2/40/60 | 102.2 9.0/42/58 |
| 6 | 101.8 9.4/44/66 | 101.8 8.7/39/61 | 102.0 11.0/39/61 | 102.3 11.3/37/63 | 101.8 9.8/41/59 |
| 7 | 101.5 . . . | 101.6 . . . | 101.5 . . . | 101.7 . . . | 101.9 . . . |
| 8 | 101.1 10.7/45/55 | 101.8 9.5/41/59 | 101.6 10.3/45/55 | 102.2 11.2/40/60 | 101.7 10.2/47/53 |
| 9 | 101.8 . . . | 101.9 . . . | 101.9 . . . | 102.7 . . . | 102.2 . . . |

FECAL HA: Titers were all less than 1:32 (generally 1:8–1:16) before and after challenge, indicating no shed of virulent (challenge) virus.

B.

SPF controls challenged with CPV-2b (passage 5):

| Post-challenge day | 1418-c Temp WBC/Ly/PMN | Weight | 1419-c Temp. WBC/Ly/PMN | Weight | Fecal HA (Pool) |
|---|---|---|---|---|---|
| 0 | 102.6 11.0/42/59 | 12.3# | 102.4 9.8/36/64 | 12# | 1:32 |
| 1 | 101.8 . . . | | 101.3 . . . | | 1:16 |
| 2 | 102.8 10.9/55/65 | | 103.0 9.5/41/59 | | 1:16 |
| 3 | 102.0 . . . | | 102.6 . . . | | 1:512 |
| 4 | 101.8 8.1/7/93 | | 103.1 8.9/10/90 | | 1:65, 536 |
| 5 | 102.6 9.2/9/91 | | 102.4 9.0/7/93 | | 1:162, 144 |
| 6 | 103.0 4.4/40/60 | | 102.6 4.5/38/62 | | no feces |
| 7 | 102.2 . . . | | 103.2 . . . | | 1:64 |
| 8 | 101.5 . . . | 10.6# | 102.2 . . . | 10.2# | 1:64 |
| 9 | 101.8 8.9/47/53 | | 101.9 8.5/40/60 | | 1:16 |
| 10 | 101.4 . . . | | 101.7 . . . | | 1:16 |

TABLE 4

SEROLOGICAL RESPONSES TO VACCINATION WITH vBI440

HI Antibody Titers (CPV-2b antigen):

| | 1411 | 1412 | 1413 | 1414 | 1415 |
|---|---|---|---|---|---|
| Pre-inoc. | <10 | <10 | <10 | <10 | <10 |
| 1 wk. PI | 2560 | 5120 | 1280 | 2560 | 2560 |
| 3 wk. PI (pre-challenge) | 5120 | 10,240 | 5120 | 10,240 | 10,240 |
| 10 days post-challenge | 5120 | 10,240 | 2560 | 2560 | 2560 |

Serology (HI antibody titer):

| | 1418-C | 1419-C |
|---|---|---|
| Prechallenge: | <10 | <10 |
| 10 days | 5120 | 5120 |
| 21 days | 10,240 | 5120 |

11. EXAMPLE: VACCINATION WITH ATTENUATED PASSAGE 65 VIRUS 12.5 week-old SPF beagle pups are vaccinated by the subcutaneous route with 1 dose ($10^5$ TCID$_{50}$/ml) of plaque cloned passage 65. Two control pups are kept in isolation until challenge with virulent CPV-39. Challenge is performed at 20 days after vaccination and consisted of inoculation with $10^{6.2}$ TCID$_{50}$ units in 3 ml of inoculum.

Pre-inoculation blood samples are taken for leukocyte counts and at intervals for 8 days post-challenge. Dogs are observed twice daily for signs of illness, including rectal temperatures. Fecal samples are also collected during the same time period and pooled samples from each isolation unit are prepared as a 10% volume suspension in phosphate-buffered saline and are then tested for virulent viral shed using an HA assay.

Blood for serological testing is obtained on post-vaccination days 0, 7 and 21 and 10 days after challenge with virulent CPV-2b. Hemagglutination-inhibition (HI) titers of the vaccinated animals are performed by collecting animal sera and diluting 1:5 in BBS, then heat inactivating at 56° C. for 30 minutes. To the sera, 0.010 ml 50% packed red blood cells are added, and the mixture is allowed to stand for 1 hour at 4° C. In a microtiter well, 0.025 ml BBS, and serial dilutions of heat-inactivated sera, beginning at 0.025 ml, are added, followed by 0.025 ml of diluted antigen. Incubation of the plates for 1 hour at room temperature is followed by the addition of 0.050 ml 0.5% RBC suspension. An antigen control is set up by setting up a parallel plate without sera. All plates are shaken and placed at 4° C. for 4–16 hours. The HI titer is the reciprocal of the highest serum dilution that completely prevents hemagglutination.

12. EXAMPLE: VACCINATION OF CATS AGAINST FPV WITH PASSAGE 65

Eight to sixteen week-old kittens are vaccinated by the subcutaneous route with 1 dose ($10^5$ $TCID_{50}$/ml) of plaque cloned passage 65. Two control kittens are kept in isolation until challenge with virulent CPV-39. Challenge is performed at 20 days after vaccination and consisted of inoculation with $10^{6.2}$ $TCID_{50}$ units in 3 ml of inoculum.

Pre-inoculation blood samples are taken for leukocyte counts and at intervals for 8 days post-challenge. cats are observed twice daily for signs of illness, including rectal temperatures. Fecal samples are also collected during the same time period and pooled samples from each isolation unit are prepared as a 10% volume suspension in phosphate-buffered saline and are then tested for virulent viral shed using an HA assay.

Blood for serological testing is obtained on post-vaccination days 0, 7 and 21 and 10 days after challenge with virulent CPV-2b. Hemagglutination-inhibition (HI) titers of the vaccinated animals are performed by collecting animal sera and diluting 1:5 in BBS, then heat inactivating at 56° C. for 30 minutes. To the sera, 0.010 ml 50% packed red blood cells are added, and the mixture is allowed to stand for 1 hour at 4° C. In a microtiter well, 0.025 ml BBS, and serial dilutions of heat-inactivated sera, beginning at 0.025 ml, are added, followed by 0.025 ml of diluted antigen. Incubation of the plates for 1 hour at room temperature is followed by the addition of 0.050 ml 0.5% RBC suspension. An antigen control is set up by setting up a parallel plate without sera. All plates are shaken and placed at 4° C. for 4–16 hours. The HI titer is the reciprocal of the highest serum dilution that completely prevents hemagglutination.

13. DEPOSIT OF MICROORGANISMS

The following microorganisms were deposited with the American Type Culture Collection (ATCC), Rockville, Md., on Oct. 28, 1994, and have been assigned the following accession numbers:

| | Accession Numbers |
|---|---|
| Virus | |
| CPV-39 passage #60 | ATCC No. VR 2491 |
| vBI440 | ATCC No. VR 2489 |
| CPV-39 passage #5 | ATCC No. VR 2490 |
| Plasmid | |
| pBI440 | ATCC No. 75938 |

The following microorganism was deposited with the American Type Culture Collection (ATCC), Rockville, Md., on May 6, 1996, and has been assigned the following accession number:

| Virus | Accession Numbers |
|---|---|
| CPV-39 passage #65 | ATCC No. VR 2528 |

The present invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those described herein will become apparent to those skilled in the art from the foregoing description and the accompanying figures. Such modifications are intended to fall within the scope of the appended claims.

A number of references are cited herein, the entire disclosures of which are incorporated herein in their entirety, by reference.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 5049 base pairs ( B ) TYPE: nucleic acid
( C ) STRANDEDNESS: both
( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Parvovirus ( x i ) SEQUENCE DESCRIPTION: SEQ ID NO:1:

| | | | | | | |
|---|---|---|---|---|---|---|
| ATCATTCTTT | AGAACCAACT | GACCAAGTTC | ACGTACGTAT | GACGTGATGA | CGCGCGCTAC | 60 |
| GCGCGCTGCC | TACGGCAGTC | ACACGTCATA | CGTACGTTCC | TTGGTCAGTT | GGTTCTAAAG | 120 |
| AATGATAGGC | GGTTTGTGTG | TTTAAACTTG | GGCGGGAAAA | GGTGGCGGGC | TAATTGTGGG | 180 |
| CGTGGTTAAA | GGTATAAAAG | ACAAACCATA | GACCGTTACT | GACATTCGCT | TCTTGTCTTT | 240 |
| GACAGAGTGA | ACCTCTCTTA | CTTTGACTAA | CCATGTCTGG | CAACCAGTAT | ACTGAGGAAG | 300 |
| TTATGGAGGG | AGTAAATTGG | TTAAAGAAAC | ATGCAGAAAA | TGAAGCATTT | TCGTTTGTTT | 360 |
| TTAAATGTGA | CAACGTCCAA | CTAAATGGAA | AGGATGTTCG | CTGGAACAAC | TATACCAAAC | 420 |
| CAATTCAAAA | TGAAGAGCTA | ACATCTTTAA | TTAGAGGAGC | ACAAACAGCA | ATGGATCAAA | 480 |
| CCGAAGAAGA | AGAAATGGAC | TGGGAATCGG | AAGTTGATAG | TCTCGCCAAA | AAGCAAGTAC | 540 |
| AAACTTTTGA | TGCATTAATT | AAAAAATGTC | TTTTTGAAGT | CTTTGTTTCT | AAAAATATAG | 600 |
| AACCAAATGA | ATGTGTTTGG | TTTATTCAAC | ATGAATGGGG | AAAAGATCAA | GGCTGGCATT | 660 |
| GTCATGTTTT | ACTTCATAGT | AAGAACTTAC | AACAAGCAAC | TGGTAAATGG | CTACGCAGAC | 720 |
| AAATGAATAT | GTATTGGAGT | AGATGGTTGG | TGACTCTTTG | TTCGGTAAAC | TTAACACCAA | 780 |
| CTGAAAAGAT | TAAGCTCAGA | GAAATTGCAG | AAGATAGTGA | ATGGGTGACT | ATATTAACAT | 840 |
| ACAGACATAA | GCAAACAAAA | AAAGACTATG | TTAAAATGGT | TCATTTGGA | AATATGATAG | 900 |
| CATATTACTT | TTTAACAAG | AAAAAAATTG | TCCACATGAC | AAAAGAAAGT | GGCTATTTTT | 960 |
| TAAGTACTGA | TTCTGGTTGG | AAATTTAACT | TTATGAAGTA | TCAAGACAGA | CAAATTGTCA | 1020 |
| GCACACTTTA | CACTGAACAA | ATGAAACCAG | AAACCGTTGA | AACCACAGTG | ACGACAGCAC | 1080 |
| AGGAAACAAA | GCGCGGGAGA | ATTCAAACTA | AAAGGAAGT | GTCAATCAAA | TGTACTTTGC | 1140 |
| GGGACTTGGT | TAGTAAAAGA | GTAACATCAC | CTGAAGACTG | GATGATGTTA | CAACCAGATA | 1200 |
| GTTATATTGA | AATGATGGCA | CAACCAGGAG | GTGAAAATCT | TTTAAAAAAT | ACACTTGAAA | 1260 |
| TTTGTACTTT | GACTTTAGCA | AGAACAAAAA | CAGCATTTGA | ATTAATACTT | GAAAAAGCAG | 1320 |
| ATAATACTAA | ACTAACTAAC | TTTGATCTTG | CAAATTCTAG | AACATGTCAA | ATTTTTAGAA | 1380 |
| TGCACGGATG | GAATTGGATT | AAAGTTTGTC | ACGCTATAGC | ATGTGTTTTA | AATAGACAAG | 1440 |
| GTGGTAAAAG | AAATACAGTT | CTTTTTCATG | GACCAGCAAG | TACAGGAAAA | TCTATCATTG | 1500 |
| CTCAAGCCAT | AGCACAAGCT | GTGGGTAATG | TTGGTTGTTA | TAATGCAGCA | AATGTAAATT | 1560 |
| TTCCATTTAA | TGACTGTACC | AATAAAAATT | TAATTTGGAT | TGAAGAAGCT | GGTAACTTTG | 1620 |
| GTCAACAAGT | TAATCAATTT | AAAGCAATCT | GTTCTGGACA | AACAATTAGA | ATTGATCAAA | 1680 |
| AAGGTAAAGG | AAGTAAGCAA | ATTGAACCAA | CTCCAGTAAT | TATGACAACT | AATGAAAATA | 1740 |
| TAACAATTGT | GAGAATTGGA | TGTGAAGAAA | GACCTGAACA | TACACAACCA | ATAAGAGACA | 1800 |
| GAATGTTGAA | CATTAAGTTA | GTATGTAAGC | TTCCAGGAGA | CTTTGGTTTG | TTGATAAAG | 1860 |
| AAGAATGGCC | TTTAATATGT | GCATGGTTAG | TTAAACATGG | TTTTGAATCA | ACCATGGCTA | 1920 |
| ACTATACACA | TCATTGGGGA | AAAGTACCAG | AATGGGATGA | AAACTGGGCG | GAGCCTAAAA | 1980 |

```
TACAAGAAGG  TATAAATTCA  CCAGGTTGCA  AAGACTTAGA  GACACAAGCG  GCAAGCAATC   2040

CTCAGAGTCA  AGACCAAGTT  CTAACTCCTC  TGACTCCGGA  CGTAGTGGAC  CTTGCACTGG   2100

AACCGTGGAG  TACTCCAGAT  ACGCCTATTG  CAGAAACTGC  AAATCAACAA  TCAAACCAAC   2160

TTGGCGTTAC  TCACAAAGAC  GTGCAAGCGA  GTCCGACGTG  GTCCGAAATA  GAGGCAGACC   2220

TGAGAGCCAT  CTTTACTTCT  GAACAATTGG  AAGAAGATTT  TCGAGACGAC  TTGGATTAAG   2280

GTACGATGGC  ACCTCCGGCA  AAGAGAGCCA  GGAGAGGTAA  GGGTGTGTTA  GTAAAGTGGG   2340

GGGAGGGGAA  AGATTTAATA  ACTTAACTAA  GTATGTGTTT  TTTTATAGGA  CTTGTGCCTC   2400

CAGGTTATAA  ATATCTTGGG  CCTGGGAACA  GTCTTGACCA  AGGAGAACCA  ACTAACCCTT   2460

CTGACGCCGC  TGCAAAAGAA  CACGACGAAG  CTTACGCTGC  TTATCTTCGC  TCTGGTAAAA   2520

ACCCATACTT  ATATTTCTCG  CCAGCAGATC  AACGCTTTAT  AGATCAAACT  AAGGACGCTA   2580

AAGATTGGGG  GGGGAAAATA  GGACATTATT  TTTTAGAGC   TAAAAGGCA   ATTGCTCCAG   2640

TATTAACTGA  TACACCAGAT  CATCCATCAA  CATCAAGACC  AACAAAACCA  ACTAAAGAA    2700

GTAAACCACC  ACCTCATATT  TTCATCAATC  TTGCAAAAAA  AAAAAAAGCC  GGTGCAGGAC   2760

AAGTAAAAAG  AGACAATCTT  GCACCAATGA  GTGATGGAGC  AGTTCAACCA  GACGGTGGTC   2820

AACCTGCTGT  CAGAAATGAA  AGAGCTACAG  GATCTGGGAA  CGGGTCTGGA  GGCGGGGGTG   2880

GTGGTGGTTC  TGGGGGTGTG  GGGATTTCTA  CGGGTACTTT  CAATAATCAG  ACGGAATTTA   2940

AATTTTTGGA  AAACGGATGG  GTGGAAATCA  CAGCAAACTC  AAGCAGACTT  GTACATTTAA   3000

ATATGCCAGA  AAGTGAAAAT  TATAGAAGAG  TGGTTGTAAA  TAATTTGGAT  AAAACTGCAG   3060

TTAACGAAAA  CATGGCTTTA  GATGATACTC  ATGCACAAAT  TGTAACACCT  TGGTCATTGG   3120

TTGATGCAAA  TGCTTGGGGA  GTTTGGTTTA  ATCCAGGAGA  TTGGCAACTA  ATTGTTAATA   3180

CTATGAGTGA  GTTGCATTTA  GTTAGTTTTG  AACAAGAAAT  TTTTAATGTT  GTTTTAAAGA   3240

CTGTTTCAGA  ATCTGCTACT  CAGCCACCAA  CTAAAGTTTA  TAATAATGAT  TTAACTGCAT   3300

CATTGATGGT  TGCATTAGAT  AGTAATAATA  CTATGCCATT  TACTCCAGCA  GCTATGAGAT   3360

CTGAGACATT  GGGTTTTTAT  CCATGGAAAC  CAACCATACC  AACTCCATGG  AGATATTATT   3420

TTCAATGGGA  TAGAACATTA  ATACCATCTC  ATACTGGAAC  TAGTGGCACA  CCAACAAATA   3480

TATACCATGG  TACAGATCCA  GATGATGTTC  AATTTTATAC  TATTGAAAAT  TCTGTGCCAG   3540

TACACTTACT  AAGAACAGGT  GATGAATTTG  CTACAGGAAC  ATTTTTTTT   GATTGTAAAC   3600

CATGTAGACT  AACACATACA  TGGCAAACAA  ATAGAGCATT  GGGCTTACCA  CCATTTCTAA   3660

ATTCTTTGCC  TCAATCTGAA  GGAGGTACTA  ACTTTGGTTA  TATAGGAGTT  CAACAAGATA   3720

AAAGACGTGG  TGTAACTCAA  ATGGGAAATA  CAAACTATAT  TACTGAAGCT  ACTATTATGA   3780

GACCAGCTGA  GGTTGGTTAT  AGTGCACCAT  ATTATTCTTT  TGAGGCGTCT  ACACAAGGGC   3840

CATTTAAAAC  ACCTATTGCA  GCAGGACGGG  GGGAGCGCA   AACAGATGAA  AATCAAGCAG   3900

CAGATGGTGA  TCCAAGATAT  GCATTTGGTA  GACAACATGG  TCAAAAAACT  ACCACAACAG   3960

GAGAAACACC  TGAGAGATTT  ACATATATAG  CACATCAAGA  TACAGGAAGA  TATCCAGAAG   4020

GAGATTGGAT  TCAAAATATT  AACTTTAACC  TTCCTGTAAC  AGATGATAAT  GTATTGCTAC   4080

CAACAGATCC  AATTGGAGGT  AAAACAGGAA  TTAACTATAC  TAATATATTT  AATACTTATG   4140

GTCCTTTAAC  TGCATTAAAT  AATGTACCAC  CAGTTTATCC  AAATGGTCAA  ATTTGGGATA   4200

AAGAATTTGA  TACTGACTTA  AAACCAAGAC  TTCATGTAAA  TGCACCATTT  GTTTGTCAAA   4260

ATAATTGTCC  TGGTCAATTA  TTTGTAAAAG  TTGCGCCTAA  TTTAACAAAT  GAATATGATC   4320

CTGATGCATC  TGCTAATATG  TCAAGAATTG  TAACTTACTC  AGATTTTTGG  TGGAAAGGTA   4380
```

-continued

| | | | | | |
|---|---|---|---|---|---|
| AATTAGTATT | TAAAGCTAAA | CTAAGAGCCT | CTCATACTTG | GAATCCAATT | CAACAAATGA | 4440
| GTATTAATGT | AGATAACCAA | TTTAACTATG | TACCAAGTAA | TATTGGAGGT | ATGAAAATTG | 4500
| TATATGAAAA | ATCTCAACTA | GCACCTAGAA | AATTATATTA | ACATACTTAC | TATGTTTTTA | 4560
| TGTTTATTAC | ATATCAACTA | GCACCTAGAA | AATTATATTA | ATATACTTAC | TATGTTTTTA | 4620
| TGTTTATTAC | ATATTATTTT | AAGATTAATT | AAATTACAGC | ATAGAAATAT | TGTACTTGTA | 4680
| TTTGATATAG | GATTTAGAAG | GTTTGTTATA | TGGTATACAA | TAACTGTAAG | AAATAGAAGA | 4740
| ACATCTAGAT | CATAGTTAGT | AGTTTGTTTT | ATAAATGTA | TTGTAAACCA | TTAATGTATG | 4800
| TTGTTATGGT | GTGGGTGGTT | GGTTGGTTTG | CCCTTAGAAT | ATGTTAAGGA | CCAAAAAAAA | 4860
| TCAATAAAAG | ACATTTAAAA | TTAAATGGCC | TCGTATACTG | TCTATAAGGT | GAACTAACCT | 4920
| TACCATAAGT | ATCAATCTGT | CTTTAAGGGG | GGGGTGGGTG | GGAGATGCAC | AACATCAGTA | 4980
| GACTGACTGG | CCTGGTTGGT | TGCTCTGCTT | AATCAACCAG | ACCGCGTAGC | GGTCTGGTTG | 5040
| ATTAAGCGC | | | | | | 5049

( 2 ) INFORMATION FOR SEQ ID NO:2:

( i ) SEQUENCE CHARACTERISTICS:
        ( A ) LENGTH: 5049 base pairs
        ( B ) TYPE: nucleic acid
        ( C ) STRANDEDNESS: both
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Parvovirus ( x i ) SEQUENCE DESCRIPTION: SEQ ID NO:2:

| | | | | | |
|---|---|---|---|---|---|
| ATCATTCTTT | AGAACCAACT | GACCAAGTTC | ACGTACGTAT | GACGTGATGA | CGCGCGCTGC | 60
| GCGCGCTGCC | TACGGCAGTC | ACACGTCATA | CGTACGCTCC | TTGGTCAGTT | GGTTCTAAAG | 120
| AATGATAGGC | GGTTTGTGTG | TTTAAACTTG | GGCGGGAAAA | GGTGGCGGGC | TAATTGTGGG | 180
| CGTGGTTAAA | GGTATAAAAG | ACAAACCATA | GACCGTTACT | GACATTCGCT | TCTTGTCTTT | 240
| GACAGAGTGA | ACCTCTCTTA | CTTTGACTAA | CCATGTCTGG | CAACCAGTAT | ACTGAGGAAG | 300
| TTATGGAGGG | AGTAAATTGG | TTAAAGAAAC | ATGCAGAAAA | TGAAGCATTT | TCGTTTGTTT | 360
| TTAAATGTGA | CAACGTCCAA | CTAAATGGAA | AGGATGTTCG | CTGGAACAAC | TATACCAAAC | 420
| CAATTCAAAA | TGAAGAGCTA | ACATCTTTAA | TTAGAGGAGC | ACAAACAGCA | ATGGATCAAA | 480
| CCGAAGAAGA | AGAAATGGAC | TGGGAATCGG | AAGTTGATAG | TCTCGCCAAA | AAGCAAGTAC | 540
| AAACTTTTGA | TGCATTAATT | AAAAAATGTC | TTTTTGAAGT | CTTTGTTTCT | AAAAATATAG | 600
| AACCAAATGA | ATGTGTTTGG | TTTATTCAAC | ATGAATGGGG | AAAAGATCAA | GGCTGGCATT | 660
| GTCATGTTTT | ACTTCATAGT | AAGAACTTAC | AACAAGCAAC | TGGTAAATGG | CTACGCAGAC | 720
| AAATGAATAT | GTATTGGAGT | AGATGGTTGG | TGACTCTTTG | TTCGGTAAAC | TTAACACCAA | 780
| CTGAAAAGAT | TAAGCTCAGA | GAAATTGCAG | AAGATAGTGA | ATGGGTGACT | ATATTAACAT | 840
| ACAGACATAA | GCAAACAAAA | AAAGACTATG | TTAAAATGGT | TCATTTTGGA | AATATGATAG | 900
| CATATTACTT | TTTAACAAAG | AAAAAAATTG | TCCACATGAC | AAAAGAAAGT | GGCTATTTTT | 960
| TAAGTACTGA | TTCTGGTTGG | AAATTTAACT | TTATGAAGTA | TCAAGACAGA | CAAATTGTCA | 1020
| GCACACTTTA | CACTGAACAA | ATGAAACCAG | AAACCGTTGA | AACCACAGTG | ACGACAGCAC | 1080

| | | | | | |
|---|---|---|---|---|---|
| AGGAAACAAA | GCGCGGGAGA | ATTCAAACTA | AAAAGGAAGT | GTCAATCAAA | TGTACTTTGC | 1140 |
| GGGACTTGGT | TAGTAAAAGA | GTAACATCAC | CTGAAGACTG | GATGATGTTA | CAACCAGATA | 1200 |
| GTTATATTGA | AATGATGGCA | CAACCAGGAG | GTGAAAATCT | TTTAAAAAAT | ACACTTGAAA | 1260 |
| TTTGTACTTT | GACTTTAGCA | AGAACAAAAA | CAGCATTTGA | ATTAATACTT | GAAAAGCAG | 1320 |
| ATAATACTAA | ACTAACTAAC | TTTGATCTTG | CAAATTCTAG | AACATGTCAA | ATTTTAGAA | 1380 |
| TGCACGGATG | GAATTGGATT | AAAGTTTGTC | ACGCTATAGC | ATGTGTTTTA | AATAGACAAG | 1440 |
| GTGGTAAAAG | AAATACAGTT | CTTTTCATG | GACCAGCAAG | TACAGGAAAA | TCTATCATTG | 1500 |
| CTCAAGCCAT | AGCACAAGCT | GTGGGTAATG | TTGGTTGTTA | TAATGCAGCA | AATGTAAATT | 1560 |
| TTCCATTTAA | TGACTGTACC | AATAAAAATT | TAATTTGGAT | TGAAGAAGCT | GGTAACTTTG | 1620 |
| GTCAACAAGT | TAATCAATTT | AAAGCAATCT | GTTCTGGACA | AACAATTAGA | ATTGATCAAA | 1680 |
| AAGGTAAAGG | AAGTAAGCAA | ATTGAACCAA | CTCCAGTAAT | TATGACAACT | AATGAAAATA | 1740 |
| TAACAATTGT | GAGAATTGGA | TGTGAAGAAA | GACCTGAACA | TACACAACCA | ATAAGAGACA | 1800 |
| GAATGTTGAA | CATTAAGTTA | GTATGTAAGC | TTCCAGGAGA | CTTTGGTTTG | GTTGATAAAG | 1860 |
| AAGAATGGCC | TTTAATATGT | GCATGGTTAG | TTAAACATGG | TTTTGAATCA | ACCATGGCTA | 1920 |
| ACTATACACA | TCATTGGGGA | AAAGTACCAG | AATGGGATGA | AAACTGGGCG | GAGCCTAAAA | 1980 |
| TACAAGAAGG | TATAAATTCA | CCAGGTTGCA | AAGACTTAGA | GACACAAGCG | GCAAGCAATC | 2040 |
| CTCAGAGTCA | AGACCAAGTT | CTAACTCCTC | TGACTCCGGA | CGTAGTGGAC | CTTGCACTGG | 2100 |
| AACCGTGGAG | TACTCCAGAT | ACGCCTATTG | CAGAAACTGC | AAATCAACAA | TCAAACCAAC | 2160 |
| TTGGCGTTAC | TCACAAAGAC | GTGCAAGCGA | GTCCGACGTG | GTCCGAAATA | GAGGCAGACC | 2220 |
| TGAGAGCCAT | CTTTACTTCT | GAACAATTGG | AAGAAGATTT | TCGAGACGAC | TTGGATTAAG | 2280 |
| GTACGATGGC | ACCTCCGGCA | AAGAGAGCCA | GGAGAGGTAA | GGGTGTGTTA | GTAAAGTGGG | 2340 |
| GGGAGGGGAA | AGATTTAATA | ACTTAACTAA | GTATGTGTTT | TTTTATAGGA | CTTGTGCCTC | 2400 |
| CAGGTTATAA | ATATCTTGGG | CCTGGGAACA | GTCTTGACCA | AGGAGAACCA | ACTAACCCTT | 2460 |
| CTGACGCCGC | TGCAAAAGAA | CACGACGAAG | CTTACGCTGC | TTATCTTCGC | TCTGGTAAAA | 2520 |
| ACCCATACTT | ATATTTCTCG | CCAGCAGATC | AACGCTTTAT | AGATCAAACT | AAGGACGCTA | 2580 |
| AAGATTGGGG | GGGGAAAATA | GGACATTATT | TTTTTAGAGC | TAAAAGGCA | ATTGCTCCAG | 2640 |
| TATTAACTGA | TACACCAGAT | CATCCATCAA | CATCAAGACC | AACAAAACCA | ACTAAAAGAA | 2700 |
| GTAAACCACC | ACCTCATATT | TTCATCAATC | TTGCAAAAAA | AAAAAAAGCC | GGTGCAGGAC | 2760 |
| AAGTAAAAAG | AGACAATCTT | GCACCAATGA | GTGATGGAGC | AGTTCAACCA | GACGGTGGTC | 2820 |
| AACCTGCTGT | CAGAAATGAA | AGAGCTACAG | GATCTGGGAA | CGGGTCTGGA | GGCGGGGGTG | 2880 |
| GTGGTGGTTC | TGGGGGTGTG | GGGATTTCTA | CGGGTACTTT | CAATAATCAG | ACGGAATTTA | 2940 |
| AATTTTTGGA | AAACGGATGG | GTGGAAATCA | CAGCAAACTC | AAGCAGACTT | GTACATTTAA | 3000 |
| ATATGCCAGA | AAGTGAAAAT | TATAGAAGAG | TGGTTGTAAA | TAATTTGGAT | AAAACTGCAG | 3060 |
| TTAACGGAAA | CATGGCTTTA | GATGATACTC | ATGCACAAAT | TGTAACACCT | TGGTCATTGG | 3120 |
| TTGATGCAAA | TGCTTGGGGA | GTTTGGTTTA | ATCCAGGAGA | TTGGCAACTA | ATTGTTAATA | 3180 |
| CTATGAGTGA | GTTGCATTTA | GTTAGTTTTG | AACAAGAAAT | TTTTAATGTT | GTTTTAAAGA | 3240 |
| CTGTTTCAGA | ATCTGCTACT | CAGCCACCAA | CTAAAGTTTA | TAATAATGAT | TTAACTGCAT | 3300 |
| CATTGATGGT | TGCATTAGAT | AGTAATAATA | CTATGCCATT | TACTCCAGCA | GCTATGAGAT | 3360 |
| CTGAGACATT | GGGTTTTTAT | CCATGGAAAC | CAACCATACC | AACTCCATGG | AGATATTATT | 3420 |
| TTCAATGGGA | TAGAACATTA | ATACCATCTC | ATACTGGAAC | TAGTGGCACA | CCAACAAATA | 3480 |

-continued

| | | | | | | |
|---|---|---|---|---|---|---|
| TATACCATGG | TACAGATCCA | GATGATGTTC | AATTTTATAC | TATTGAAAAT | TCTGTGCCAG | 3540 |
| TACACTTACT | AAGAACAGGT | GATGAATTTG | CTACAGGAAC | ATTTTTTTT | GATTGTAAAC | 3600 |
| CATGTAGACT | AACACATACA | TGGCAAACAA | ATAGAGCATT | GGGCTTACCA | CCATTTCTAA | 3660 |
| ATTCTTTGCC | TCAATCTGAA | GGAGGTACTA | ACTTTGGTTA | TATAGGAGTT | CAACAAGATA | 3720 |
| AAAGACGTGG | TGTAACTCAA | ATGGGAAATA | CAAACTATAT | TACTGAAGCT | ACTATTATGA | 3780 |
| GACCAGCTGA | GGTTGGTTAT | AGTGCACCAT | ATTATTCTTT | TGAGGCGTCT | ACACAAGGGC | 3840 |
| CATTTAAAAC | ACCTATTGCA | GCAGGACGGG | GGGAGCGCA | AACAGATGAA | AATCAAGCAG | 3900 |
| CAGATGGTGA | TCCAAGATAT | GCATTGGTA | GACAACATGG | TCAAAAAACT | ACCACAACAG | 3960 |
| GAGAAACACC | TGAGAGATTT | ACATATATAG | CACATCAAGA | TACAGGAAGA | TATCCAGAAG | 4020 |
| GAGATTGGAT | TCAAAATATT | AACTTTAACC | TTCCTGTAAC | AGATGATAAT | GTATTGCTAC | 4080 |
| CAACAGATCC | AATTGGAGGT | AAAACAGGAA | TTAACTATAC | TAATATATTT | AATACTTATG | 4140 |
| GTCCTTTAAC | TGCATTAAAT | AATGTACCAC | CAGTTTATCC | AAATGGTCAA | ATTTGGGATA | 4200 |
| AAGAATTTGA | TACTGACTTA | AAACCAAGAC | TTCATGTAAA | TGCACCATTT | GTTTGTCAAA | 4260 |
| ATAATTGTCC | TGGTCAATTA | TTTGTAAAAG | TTGCGCCTAA | TTTAACAAAT | GAATATGATC | 4320 |
| CTGATGCATC | TGCTAATATG | TCAAGAATTG | TAACTTACTC | AGATTTTTGG | TGGAAAGGTA | 4380 |
| AATTAGTATT | TAAAGCTAAA | CTAAGAGCCT | CTCATACTTG | GAATCCAATT | CAACAAATGA | 4440 |
| GTATTAATGT | AGATAACCAA | TTTAACTATG | TACCAAGTAA | TATTGGAGGT | ATGAAAATTG | 4500 |
| TATATGAAAA | ATCTCAACTA | GCACCTAGAA | AATTATATTA | ACATACTTAC | TATGTTTTA | 4560 |
| TGTTTATTAC | ATATCAACTA | GCACCTAGAA | AATTATATTA | ATATACTTAC | TATGTTTTA | 4620 |
| TGTTTATTAC | ATATTATTTT | AAGATTAATT | AAATTACAGC | ATAGAAATAT | TGTACTTGTA | 4680 |
| TTTGATATAG | GATTTAGAAG | GTTTGTTATA | TGGTATACAA | TAACTGTAAG | AAATAGAAGA | 4740 |
| ACATTTAGAT | CATAGTTAGT | AGTTTGTTTT | ATAAAATGTA | TTGTAAACCA | TTAATGTATG | 4800 |
| TTGTTATGGT | GTGGGTGGTT | GGTTGGTTTG | CCCTTAGAAT | ATGTTAAGGA | CCAAAAAAAA | 4860 |
| TCAATAAAAG | ACATTTAAAA | CTAAATGGCC | TCGTATACTG | TCTATAAGGT | GAACTAACCT | 4920 |
| TACCATAAGT | ATCAATCTGT | CTTTAAGGGG | GGGGTGGGTG | GGAGATGCAC | AACATCAGTA | 4980 |
| GACTGACTGG | CCTGGTTGGT | TGCTCTGCTT | AATCAACCAG | ACCGCGTAGC | GGTCTGGTTG | 5040 |
| ATTAAGCGC | | | | | | 5049 |

What is claimed is:

1. The virus derived from the 65th passage of CPV-39, deposited as ATCC Deposit No. VR2528.

2. A vaccine, comprising the virus of claim 1, and a pharmaceutically acceptable carrier.

3. A method of protecting an animal susceptible to being infected with canine parvovirus from canine parvovirus disease comprising inoculating the animal with an effective amount of the vaccine of claim 2.

4. The method of claim 3 in which the vaccine is administered by an oral, nasal, intramuscular, intradermal, intravenous, or subcutaneous route.

5. The method of claim 3 in which the vaccine is administered at a dose from about $10^2$ TCID$_{50}$ to about $10^7$ TCID$_{50}$.

6. The method of claim 3 in which the vaccine is administered at a dose greater than about $10^7$ TCID$_{50}$.

7. The method of claim 3 in which the animals are wild or domestic dogs.

8. A method of protecting an animal susceptible to being infected with feline panleukopenia virus from feline leukopenia disease comprising inoculating the animal with an effective amount of the vaccine of claim 2.

9. The method of claim 8 in which the vaccine is administered by an oral, nasal, intramuscular, intradermal, intravenous, or subcutaneous route.

10. The method of claim 8 in which the vaccine is administered at a dose from about $10^2$ TCID$_{50}$ to about $10^7$ TCID$_{50}$.

11. The method of claim 8 in which the vaccine is administered at a dose greater than about $10^7$ TCID$_{50}$.

12. The method of claim 8 in which the animals are wild or domestic cats.

* * * * *